(12) United States Patent
Kurtz et al.

(10) Patent No.: US 10,406,352 B2
(45) Date of Patent: *Sep. 10, 2019

(54) SYSTEM FOR TEMPORARY NONPHARMACOLOGIC CONSTRICTION OF THE PUPIL

(71) Applicants: Ronald Michael Kurtz, Irvine, CA (US); Gergely T. Zimanyi, Berkeley, CA (US)

(72) Inventors: Ronald Michael Kurtz, Irvine, CA (US); Gergely T. Zimanyi, Berkeley, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/293,269

(22) Filed: Oct. 13, 2016

(65) Prior Publication Data
US 2018/0104477 A1 Apr. 19, 2018

(51) Int. Cl.
*A61F 9/007* (2006.01)
*A61F 9/008* (2006.01)
*A61N 5/00* (2006.01)
*A61B 18/00* (2006.01)
*A61N 1/05* (2006.01)
*A61B 3/00* (2006.01)

(52) U.S. Cl.
CPC ............ *A61N 1/0551* (2013.01); *A61B 18/00* (2013.01); *A61F 9/007* (2013.01); *A61F 9/008* (2013.01); *A61F 9/0079* (2013.01); *A61N 5/00* (2013.01); *A61B 3/0008* (2013.01); *A61B 2018/00696* (2013.01); *A61B 2018/00714* (2013.01); *A61F 2009/00844* (2013.01); *A61F 2009/00876* (2013.01); *A61F 2009/00895* (2013.01)

(58) Field of Classification Search
None
See application file for complete search history.

(56) References Cited

U.S. PATENT DOCUMENTS

| 4,770,172 A | * | 9/1988 | L'Esperance, Jr. ......................... A61F 9/00804 606/5 |
| 4,850,691 A | * | 7/1989 | Gardner ................. A61B 3/112 351/210 |
| 5,324,281 A | * | 6/1994 | Muller .................... A61F 9/008 219/121.6 |
| 5,486,880 A | * | 1/1996 | House .................. A61B 3/0008 351/158 |

(Continued)

FOREIGN PATENT DOCUMENTS

WO   WO 2015/054672 A1   4/2015

*Primary Examiner* — Carl H Layno
*Assistant Examiner* — Manolis Pahakis

(57) ABSTRACT

An ophthalmic stimulator for temporarily constricting a pupil of an eye comprises an irradiation control system, to generate an irradiation control signal, an irradiation source, coupled to the irradiation control system, to generate an irradiation, and an irradiation delivery system, coupled to the irradiation control system, to receive the irradiation from the irradiation source, and to deliver a patterned irradiation to an iris of the eye, wherein the irradiation control system controls at least one of the irradiation source and the irradiation delivery system with the irradiation control signal so that the patterned irradiation causes a temporary constriction of the pupil of the eye, without causing a permanent constriction of the pupil.

14 Claims, 38 Drawing Sheets

(56) References Cited

U.S. PATENT DOCUMENTS

| | | | |
|---|---|---|---|
| 5,649,922 A * | 7/1997 | Yavitz | A61F 9/00821 606/4 |
| 5,704,369 A * | 1/1998 | Scinto | A61B 3/112 600/558 |
| 6,004,313 A * | 12/1999 | Shimmick | A61F 9/008 351/205 |
| 6,116,736 A * | 9/2000 | Stark | A61B 3/112 351/206 |
| 6,491,688 B1 * | 12/2002 | Lin | A61F 9/008 606/4 |
| 6,679,855 B2 | 1/2004 | Horn et al. | |
| 6,682,196 B2 | 1/2004 | Sheets, Jr. et al. | |
| 6,820,979 B1 | 11/2004 | Stark et al. | |
| 7,261,412 B2 * | 8/2007 | Somani | A61F 9/00 351/159.74 |
| 7,901,071 B1 * | 3/2011 | Kulas | G02C 11/04 351/158 |
| 8,529,559 B2 | 9/2013 | Liang | |
| 9,345,549 B2 | 5/2016 | Hickenbotham | |
| 9,717,404 B1 * | 8/2017 | Brauner | G02C 7/02 |
| 9,980,642 B2 * | 5/2018 | Finkel | A61B 3/112 |
| 2002/0099305 A1 * | 7/2002 | Fukushima | A61B 3/112 600/558 |
| 2002/0135737 A1 * | 9/2002 | Petrali | A61B 3/063 351/223 |
| 2004/0243113 A1 | 12/2004 | Sugiura et al. | |
| 2005/0195360 A1 | 9/2005 | Akita et al. | |
| 2006/0084948 A1 | 4/2006 | Rovati et al. | |
| 2006/0092376 A1 | 5/2006 | Baek et al. | |
| 2006/0217691 A1 * | 9/2006 | Schuele | A61F 9/008 606/12 |
| 2006/0224146 A1 * | 10/2006 | Lin | A61F 9/008 606/4 |
| 2007/0025118 A1 * | 2/2007 | Silver | G02C 11/04 362/552 |
| 2008/0161716 A1 * | 7/2008 | Livne | A61N 1/36046 600/558 |
| 2008/0243005 A1 | 10/2008 | Jung et al. | |
| 2009/0153797 A1 | 6/2009 | Allon et al. | |
| 2009/0234336 A1 | 9/2009 | Chernyak et al. | |
| 2010/0016395 A1 * | 1/2010 | Benozzi | A61K 31/17 514/397 |
| 2011/0118598 A1 * | 5/2011 | Gertner | A61B 8/06 600/431 |
| 2011/0160622 A1 * | 6/2011 | McArdle | A61F 9/00825 601/2 |
| 2012/0242956 A1 * | 9/2012 | Chernyak | A61B 3/112 351/210 |
| 2012/0293643 A1 * | 11/2012 | Hanna | H04N 5/23212 348/78 |
| 2013/0226161 A1 * | 8/2013 | Hickenbotham | A61F 9/008 606/5 |
| 2013/0237971 A1 | 9/2013 | Raksi | |
| 2013/0289450 A1 * | 10/2013 | Homer | A61F 9/008 601/2 |
| 2014/0078468 A1 | 3/2014 | Bublitz et al. | |
| 2014/0148737 A1 * | 5/2014 | Homer | A61F 9/008 601/15 |
| 2014/0307077 A1 * | 10/2014 | Prabhakar | G06K 9/00604 348/78 |
| 2014/0336618 A1 * | 11/2014 | Wilkerson | A61F 9/0008 604/521 |
| 2015/0223682 A1 * | 8/2015 | Kamkar | A61B 3/112 351/206 |
| 2015/0245766 A1 * | 9/2015 | Rennaker | A61B 3/112 351/210 |
| 2015/0265463 A1 | 9/2015 | Hoegele et al. | |
| 2016/0166146 A1 | 6/2016 | Sarkar | |
| 2016/0198946 A1 | 7/2016 | Zhou | |
| 2016/0262611 A1 * | 9/2016 | Rotenstreich | A61B 3/14 |

* cited by examiner

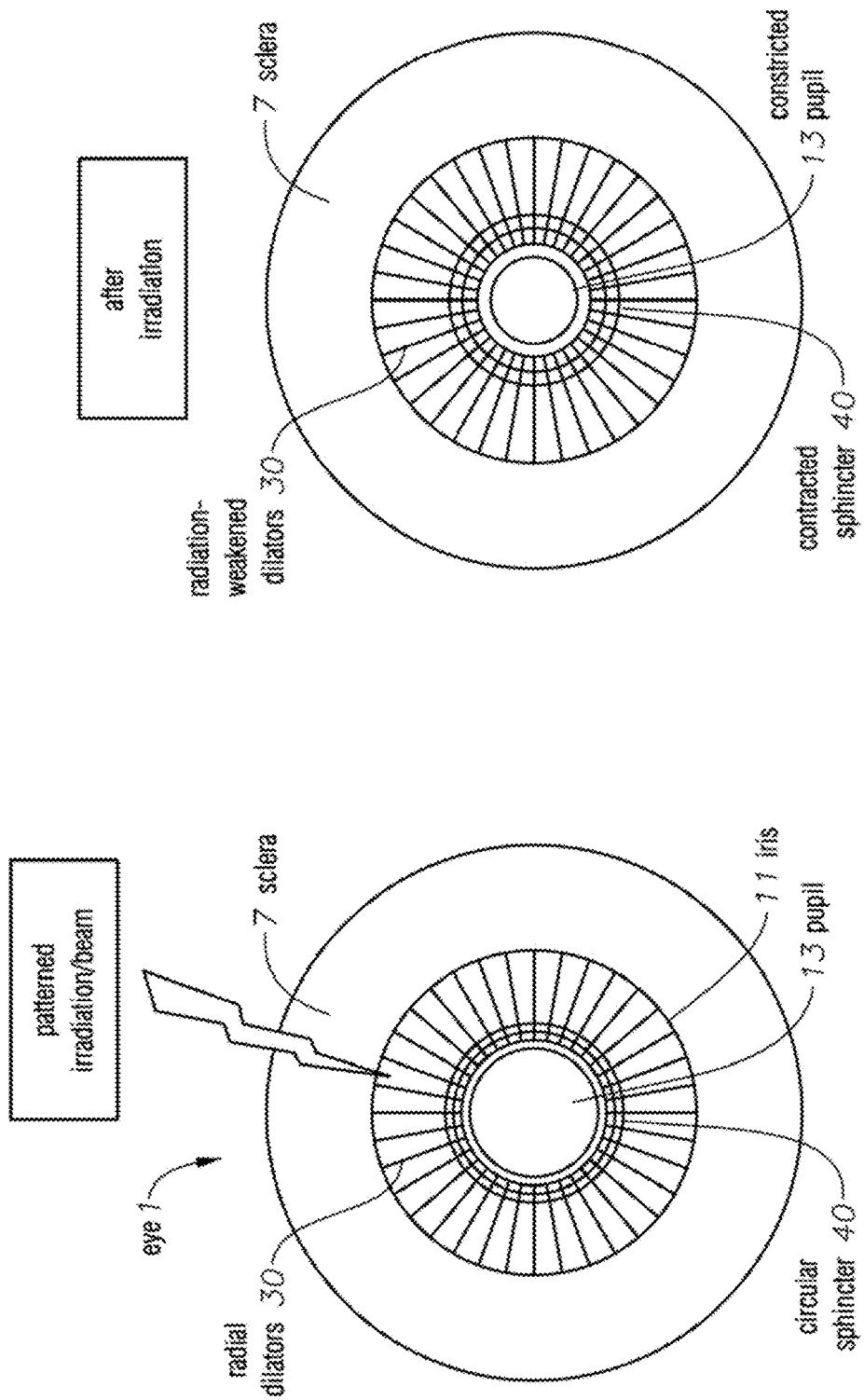

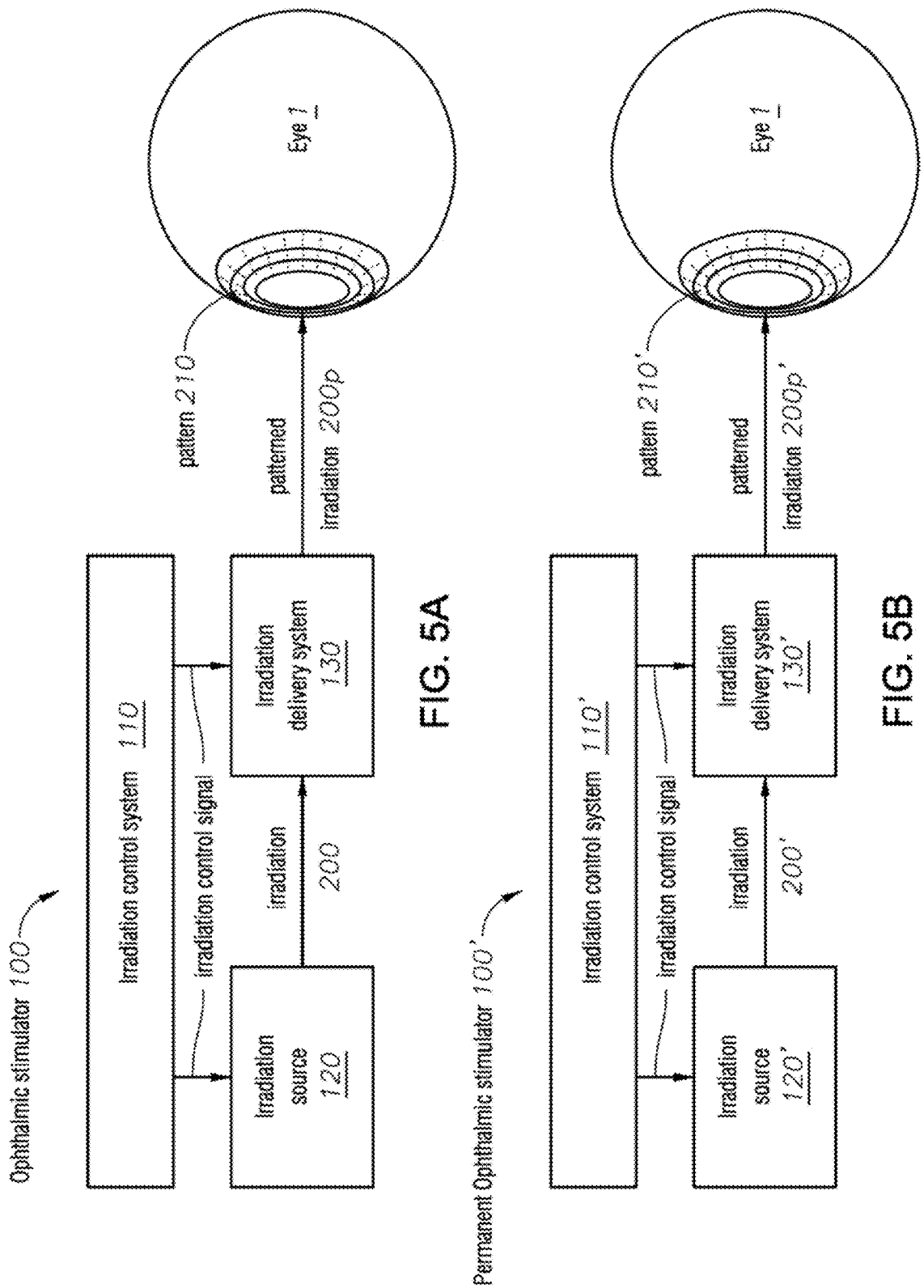

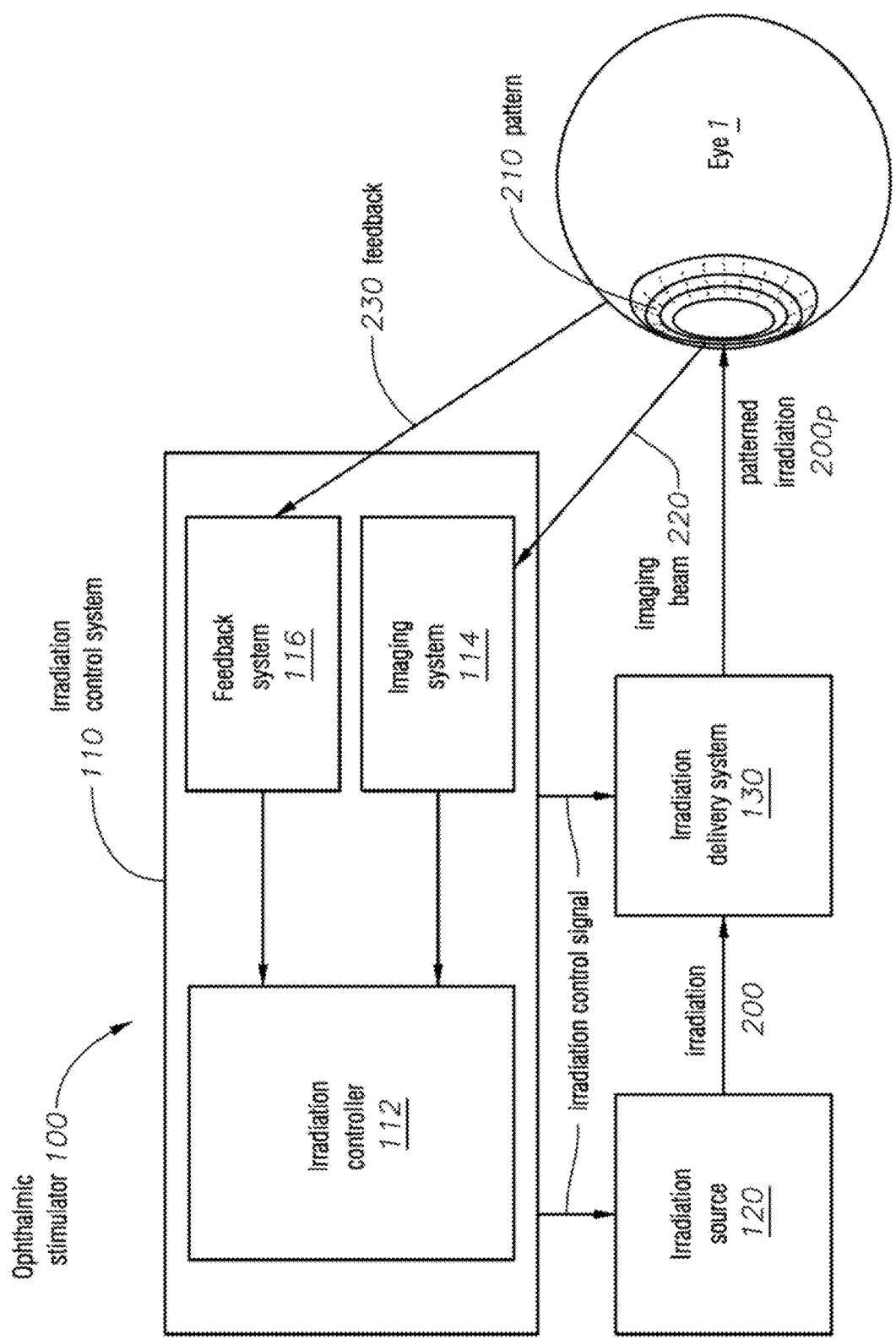

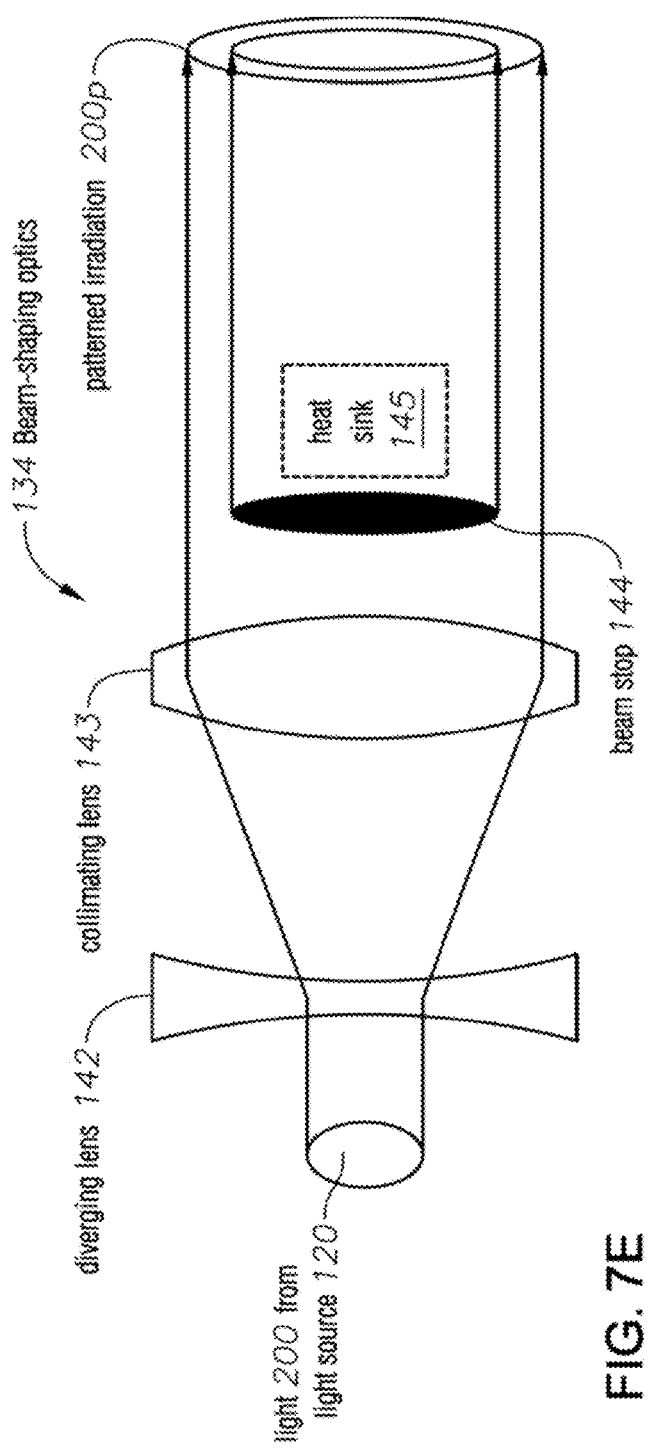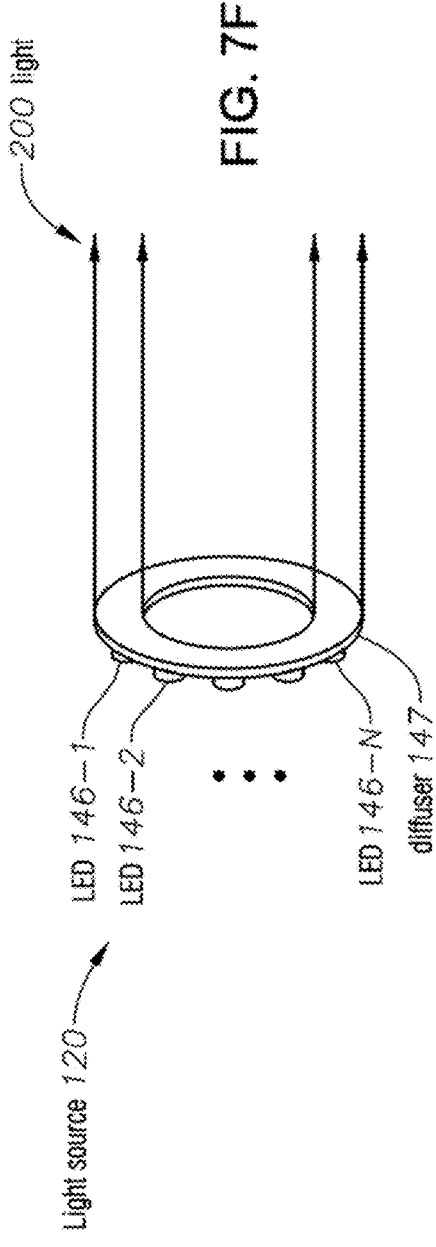
FIG. 7E
FIG. 7F

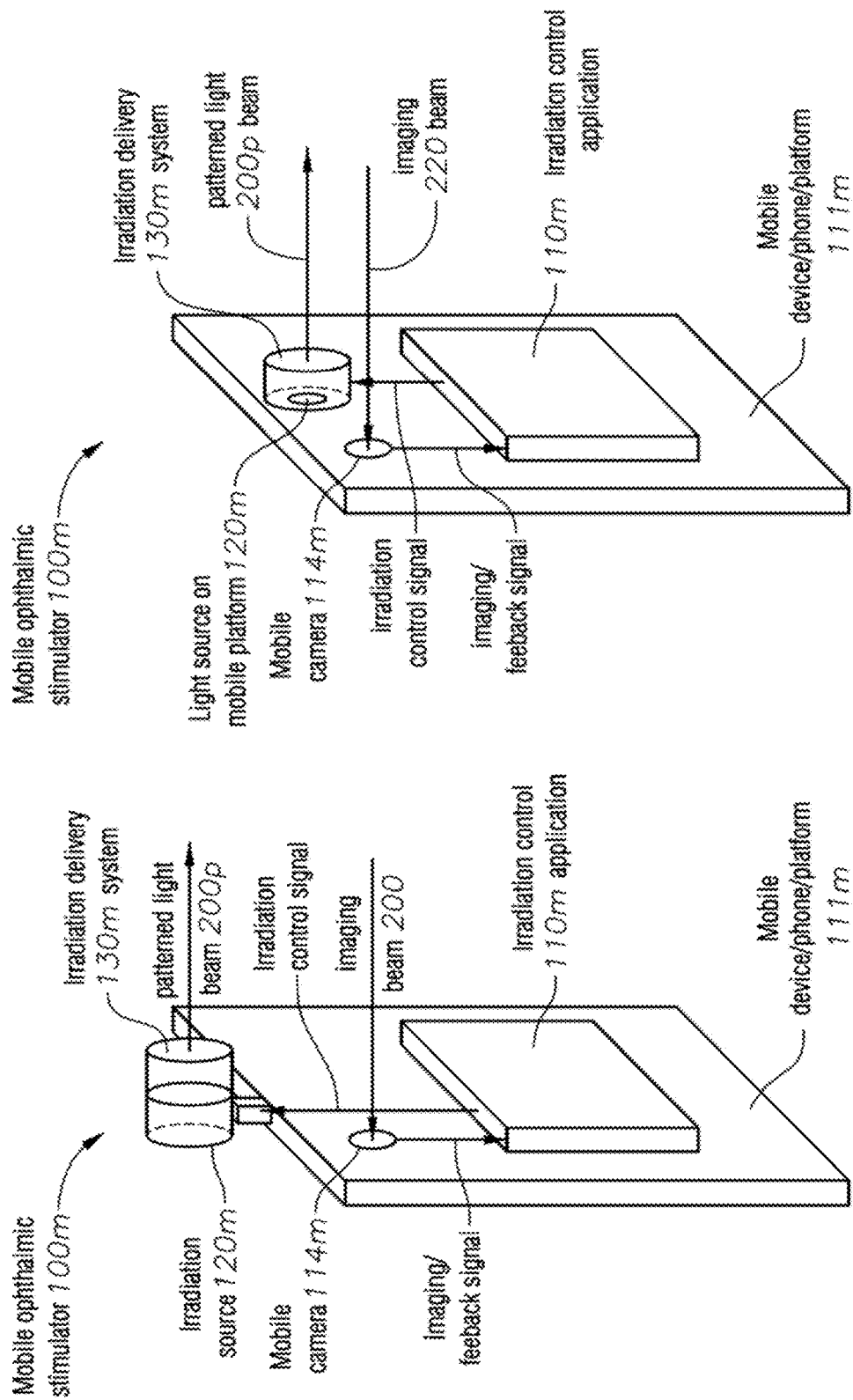

US 10,406,352 B2

SYSTEM FOR TEMPORARY NONPHARMACOLOGIC CONSTRICTION OF THE PUPIL

FIELD OF INVENTION

This invention relates to a system for pupil constriction, more precisely, to a system of temporary, non-pharmacological construction of a pupil of an eye.

BACKGROUND

A number of devices that make use of the increased depth of field of a small aperture have been proposed for use in ophthalmology, and developed to improve vision. These devices are particularly promising to improve near vision for those who have presbyopia. Examples of such devices include small aperture corneal inlays, reduced-aperture intraocular lenses, as well as other aperture implants that axe meant to impact light propagation along the visual axis. While effective, these surgically implanted permanent inlays carry the risk inherent with any implantable device, such as inflammation, infection, or displacement that may require secondary surgical procedures to remove the implant and may necessitate performing other procedures.

Pharmacological methods have also been proposed using medications such as pilocarpine and other agents to temporarily constrict the pupil. While these drugs can temporarily improve vision, they generally require frequent instillation of drops, and can be associated with undesirable side effects, such as headaches.

An alternative approach has been proposed by Hickenbotham in US patent application 2013/0226161, which utilizes a laser to cauterize certain portions of the iris to cause a permanent constriction of the pupil. While this approach offers some advantages over implants and medications, the permanent constriction of the pupil, achieved by a controlled damaging of the iris dilator muscle, does not allow for a trial of the effect, and once performed, leaves the patient with a permanent deficit in iris function. In addition, the exact shape of the constricted pupil may be difficult to control, and may result in odd, irregular, oval, or other undesired pupil shapes. Therefore, the medical need persists to develop a non-pharmacological, non-permanent vision improvement that does not involve inserting a small-aperture object surgically into the eye.

In some embodiments, an ophthalmic stimulator for temporarily constricting a pupil of an eye comprises an irradiation control system, to generate an irradiation control signal; an irradiation source, coupled to the irradiation control system, to generate an irradiation; and an irradiation delivery system, coupled to the irradiation control system, to receive the irradiation from the irradiation source, and to deliver a patterned irradiation to an iris of the eye; wherein the irradiation control system controls at least one of the irradiation source and the irradiation delivery system with the irradiation control signal so that the patterned irradiation causes a temporary constriction of the pupil of the eye, without causing a permanent constriction of the pupil.

In some embodiments, a method for temporarily constricting a pupil of an eye by an ophthalmic stimulator comprises generating an irradiation control signal by an irradiation control system; generating an irradiation by an irradiation source, coupled to the irradiation control system; receiving the irradiation and delivering a patterned irradiation to an iris of the eye with an irradiation delivery system; and controlling at least one of the irradiation source and the irradiation delivery system by the irradiation control signal of the irradiation control system so that the patterned irradiation is causing a temporary constriction of the pupil of the eye, without causing a permanent constriction of the pupil.

In some embodiments, an ophthalmic stimulator for constricting a pupil of an eye comprises an irradiation control system, to generate an irradiation control signal; an irradiation source, coupled to the irradiation control system, to generate an irradiation; and an irradiation delivery system, coupled to the irradiation control system, to receive the irradiation from the irradiation source, and to deliver a patterned irradiation to an iris of the eye; wherein the irradiation control system controls at least one of the irradiation source and the irradiation delivery system with the irradiation control signal so that the patterned irradiation causes a long-term constriction of the pupil of the eye.

In some embodiments, an ophthalmic stimulator for temporarily constricting a pupil of an eye comprises an irradiation control system, to generate an irradiation control signal; a light source, coupled to the irradiation control system, to generate a light beam; and a beam-shaping optics, coupled to the irradiation control system, to receive the light beam from the light source, and to deliver a light ring to an iris of the eye; wherein the irradiation control system controls at least one of the light source and the beam-shaping optics with the irradiation control signal so that the light ring causes a temporary constriction of the pupil of the eye, without causing a permanent constriction of the pupil.

In some embodiments, an ophthalmic stimulator for temporarily constricting a pupil of an eye comprises a digital beam controller, to generate a digital beam-control signal; a light source, coupled to the beam controller, to generate a light beam; and a digitally controlled beam modulator, to receive the digital beam-control signal from the beam controller, to receive the light beam from the light source, and to modulate the received light beam into a patterned light, delivered to an iris of the eye; wherein the beam controller controls at least one of the light source and the digitally controlled beam modulator with the digital beam-control signal so that the patterned light causes a temporary constriction of the pupil of the eye, without causing a permanent constriction of the pupil.

In some embodiments, an ophthalmic stimulator for temporarily constricting a pupil of an eye comprises an irradiation control system, having a feedback system, to generate an irradiation control signal using a feedback of the feedback system; an irradiation source, coupled to the irradiation control system, to generate an irradiation; and an irradiation delivery system, having a targeting system and coupled to the irradiation control system, to receive the irradiation from the irradiation source, and to direct a patterned irradiation in a pattern to a treatment region of an iris of the eye using the targeting system; wherein the irradiation control system controls at least one of the irradiation source and the irradiation delivery system with the irradiation control signal so that the patterned irradiation causes a temporary constriction of the pupil, without causing a permanent constriction of the pupil.

In some embodiments, an ophthalmic stimulator for temporarily constricting a pupil of an eye comprises a mobile irradiation control system, to generate an irradiation control signal; an irradiation source, coupled to the irradiation control system, to generate an irradiation; and an irradiation delivery system, coupled to the mobile irradiation control system, to receive the irradiation from the irradiation source, and to deliver a patterned irradiation to an iris of the eye; wherein the mobile irradiation control system controls at least one of the irradiation source and the irradiation delivery system with the irradiation control signal so that the patterned irradiation causes a temporary constriction of the pupil of the eye, without causing a permanent constriction of the pupil.

In some embodiments, a networked system of ophthalmic stimulators for temporarily constricting eye-pupils comprises a set of ophthalmic stimulators, each ophthalmic stimulator including a mobile irradiation control system, to generate an irradiation control signal; an irradiation source, coupled to the irradiation control system, to generate an irradiation; and an irradiation delivery system, coupled to the mobile irradiation control system, to receive the irradiation from the irradiation source, and to deliver a patterned irradiation to an iris of the eye; wherein the mobile irradiation control system controls at least one of the irradiation source and the irradiation delivery system with the irradiation control signal so that the patterned irradiation causes a temporary constriction of the pupil of the eye, without causing a permanent constriction of the pupil; and a central station, including a central image processor, wherein the mobile irradiation control systems of the of the ophthalmic stimulators and the central station are configured to communicate through a communication network.

BRIEF DESCRIPTION OF THE FIGURES

FIGS. 3A-B illustrate an effect of applying an irradiation to the iris.

FIGS. 5A-B illustrate embodiments of the ophthalmic stimulator 100 and the permanent ophthalmic stimulator 100'.

FIGS. 6A-D illustrate embodiments of the ophthalmic stimulator 100.

FIGS. 7A-F illustrate embodiments of the ophthalmic stimulator 100 with a beam shaping optics 134.

FIGS. 13A-C illustrate mobile embodiment of the ophthalmic stimulator 100.

DETAILED DESCRIPTION

Embodiments of the invention address the above described needs in the following manner. Some embodiments provide systems and methods for a temporary constriction of the pupil without the need of medication therapy. The duration of the constriction can be controlled by a selection of treatment parameters. In a suitable range of treatment parameters, the procedure can be fully reversible: after a characteristic time, the pupils return to essentially their original diameter without further treatment. The pupils can be re-constricted by applying the treatment repeatedly. Therefore, the here-described methods and devices provide the advantages of a temporary, but long lasting vision improvement, while avoid the hazards associated with (1) aperture implants and inlays, inserted by a surgical procedure, (2) permanent destruction of tissue, and (3) pharmaceutical approaches and their undesirable side-effects.

Some embodiments achieve these advantages by heating the iris by an irradiation to a suitable temperature range, (1) to cause a temporary inactivation of the iris dilator muscle, and, in some cases, (2) to enhance an action of the iris constrictor sphincter muscle. This irradiative heat treatment can be applied for a time sufficiently long to cause a reduction in contractile activity, but short enough to avoid causing permanent tissue damage. While the detailed mode of action is yet to be clarified, this effect may be mediated by inactivation of the actin-myosin complex in the exposed muscle.

Figure 1:
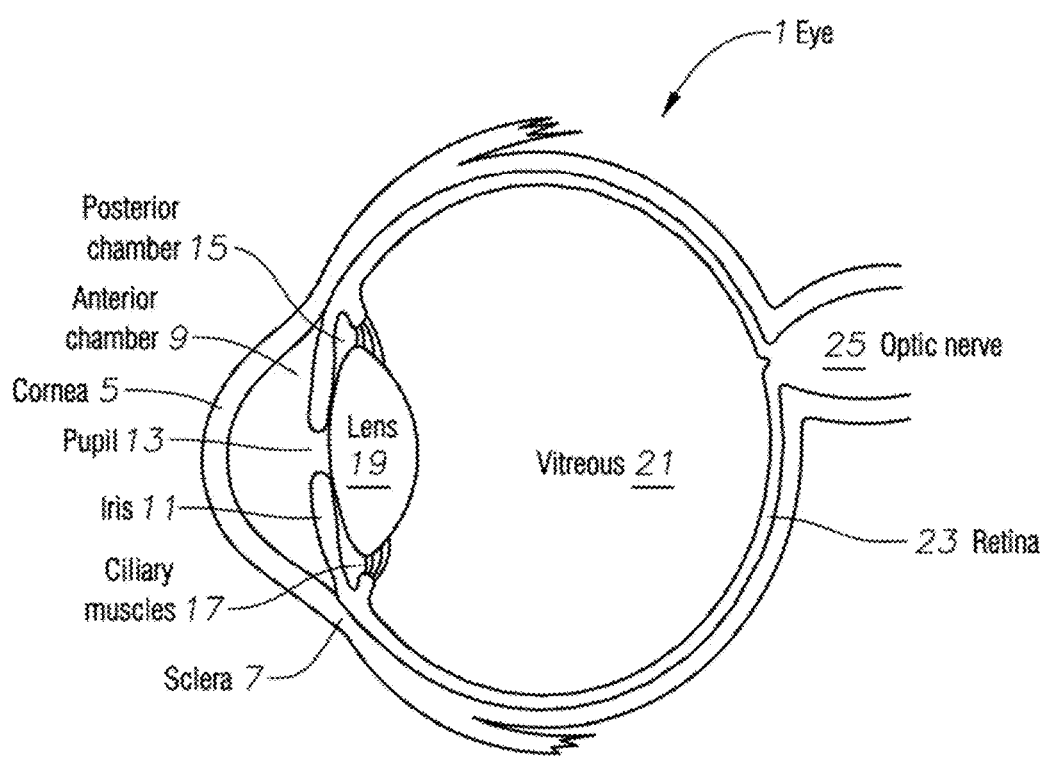
FIG. 1 illustrates an eye 1.

FIG. 1 shows a cross section of an eye 1. The eye 1 includes the well known constituents: a cornea 5, where light enters the eye 1 and a sclera 7, an opaque, fibrous protective outer layer of the eye 1 that contains collagen and elastic fibers. Distal to the cornea 5 is an anterior chamber 9 that contains an aqueous humor. The anterior chamber 9 is separated from a posterior chamber 15 by an iris 11. An opening at a center of the iris 11 is a pupil 13 that allows the light to proceed toward the posterior segment of the eye 1. Behind the pupil 13, ciliary muscles 17 hold a lens 19 in a central position. These ciliary muscles 17 can also delimit the lens 19 as pail of accommodating the vision to the distance of the target the eye is looking at. With advancing age, the ciliary muscles 17 slowly loose their ability to deform and adapt the lens 19 to varying vision distances: a condition typically referred to as presbyopia. Behind the lens 19 is a vitreous 21. As the light crosses the vitreous 21, it eventually hits the retina 23. The electric stimuli, generated by the incoming fight in the retina 23, are transmitted by the optic nerve 25 towards the brain.

Figure 2A:
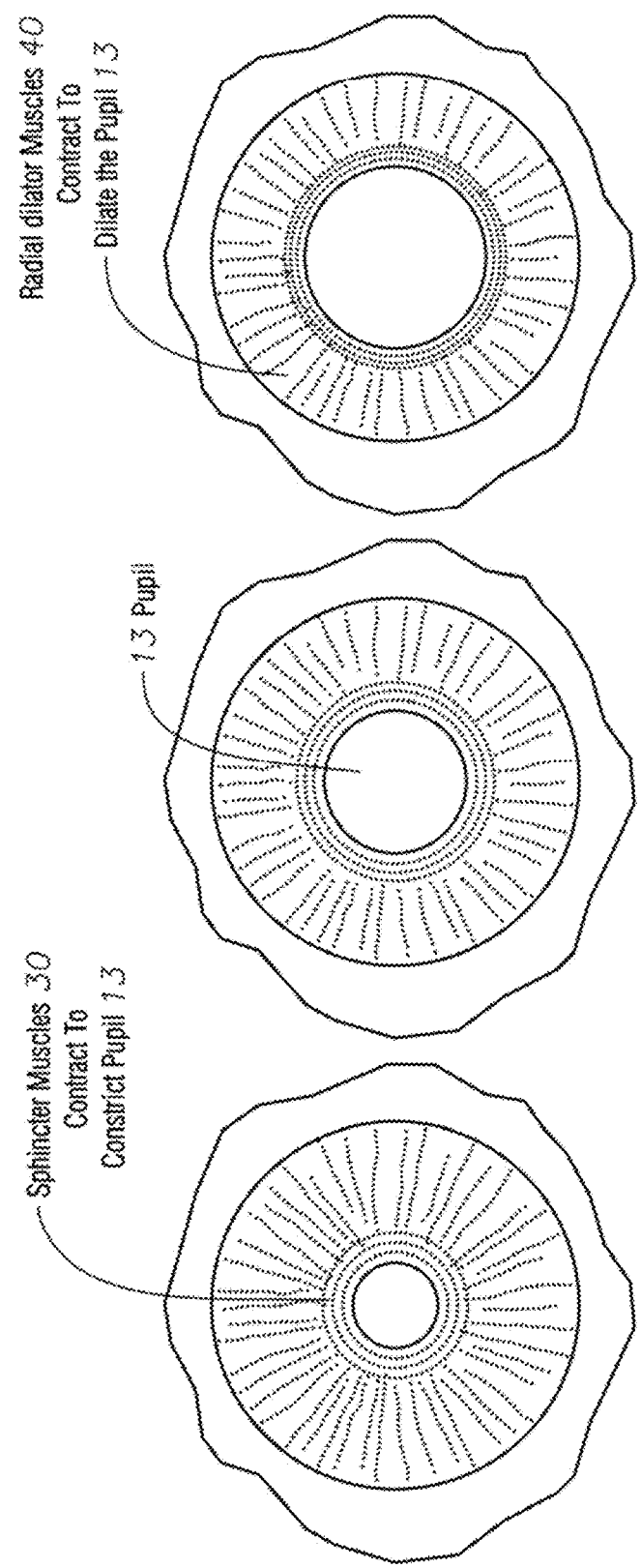
FIGS. 2A-B illustrate the pupil under different illuminations.
Figure 2B:
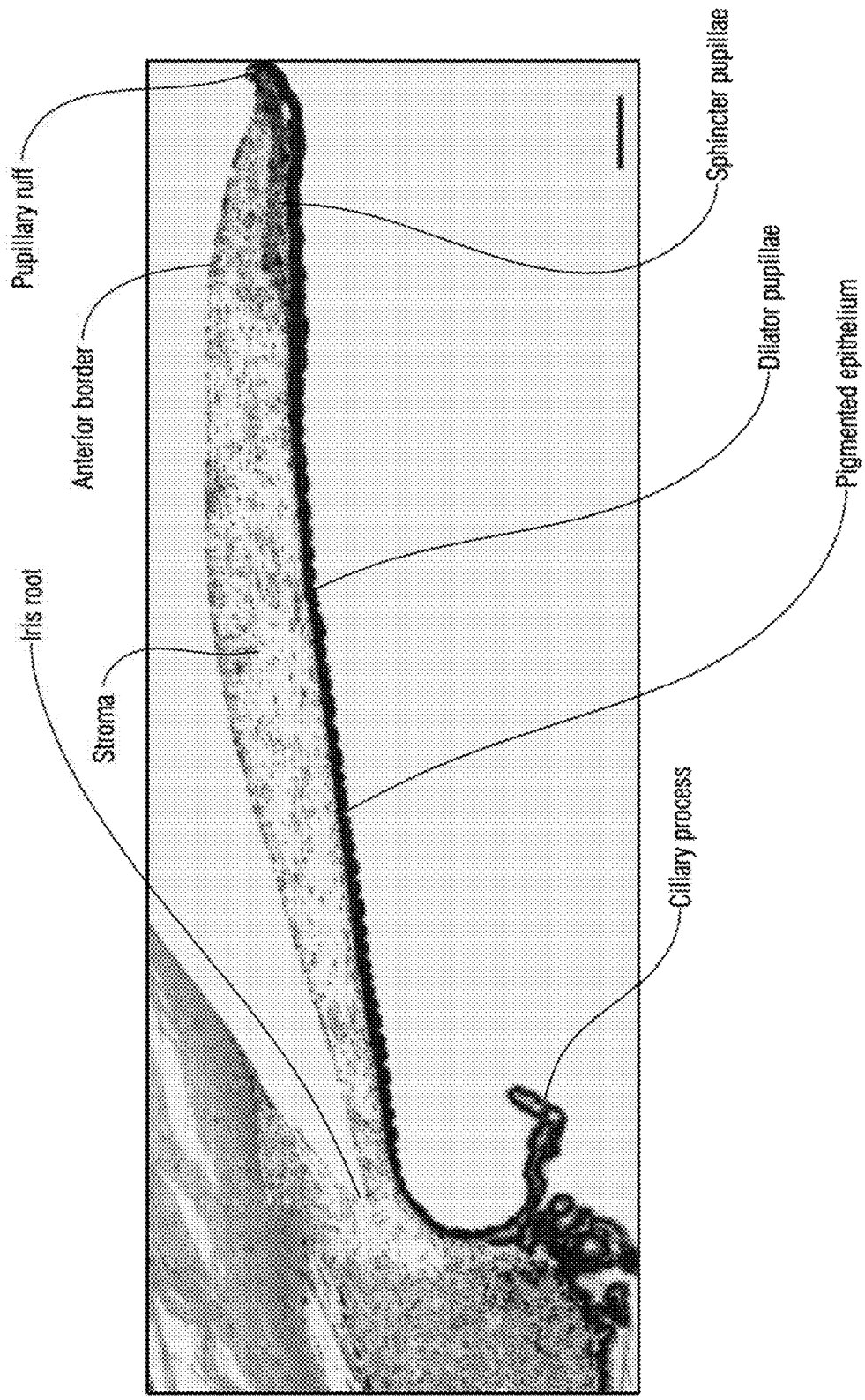

FIG. 2A-B illustrate that the iris 11 includes a circular sphincter muscle 30 around the pupil 13, capable of shrinking the perimeter of the pupil 13, thus constricting it. At the same time, the iris 11 also includes radial dilator muscles 40 that specialize in expanding, or enlarging, the pupil 13. The competition of the sphincter muscles 30 and dilator muscles 40 determines the eventual radius of the pupil 13. FIG. 2A illustrates in its left panel that in strong light the contracting sphincter muscles 30 constrict the pupil 13. FIG. 2A illustrates in its middle panel the pupil 13 in an average light. FIG. 2A illustrates in its right panel that in low light conditions, the radial dilator muscles 40 dominate the sphincter muscles 30 and dilate the pupil to enhance the amount of light directed to the retina 23.

FIG. 2B illustrates a cross section of the iris 11 from the side. It is well visible that the sphincter pupillae 30 is positioned along the edge of the pupil 13, the pupillary ruff, while the dilator pupillae 40 are located radially outward, farther from the edge of the pupil 13.

The anatomy of the muscles of the iris 11 is also important. The dilator muscle 40 fibers are typically located near the distal portion of the iris 11, adjacent to the iris pigmented epithelium. In contrast, the constrictor sphincter muscles 30 are more superficial and central, located towards the pupil's edge or margin. Details of the anatomy of these muscles can be found in much greater detail in Junqueira L. C., Carneiro 2005. Basic Histology, Eleventh Edition. The McGraw-Hill Companies, Inc. United States of America.

FIGS. 3A-B illustrate a principle of embodiments of the invention. FIG. 3A illustrates that a patterned irradiation can be applied to the iris 11 for a limited time period, such as 1-100 seconds, with less time required when higher temperatures are applied. The pattern is typically a ring of light, or light-ring. The irradiation raises the temperature of the iris 11 in a treatment region. The tissue of the iris 11 can be heated to temperatures that are not sufficient to cauterize or destroy the tissue, but are capable of reducing an activity, or responsiveness of the targeted tissues.

FIG. 3B illustrates the outcome of the irradiation. The heat treatment reduces the activity of the iris dilator muscle and this allows the pupillary constrictor, or sphincter, muscle to reduce the pupil's diameter. Reducing the pupil's diameter reduces the aberrations of the imaging of the eye, sometimes referred to as the pinhole effect in optics. Reducing the aberrations extends the depth of focus, and thereby compensates the emergence of presbyopia in an aging eye. Since this method utilizes the natural constrictor muscle to effect the pupil size change, the risk of pupil de-centration is less than in the case of surgical implants, discussed previously.

Figure 4A:
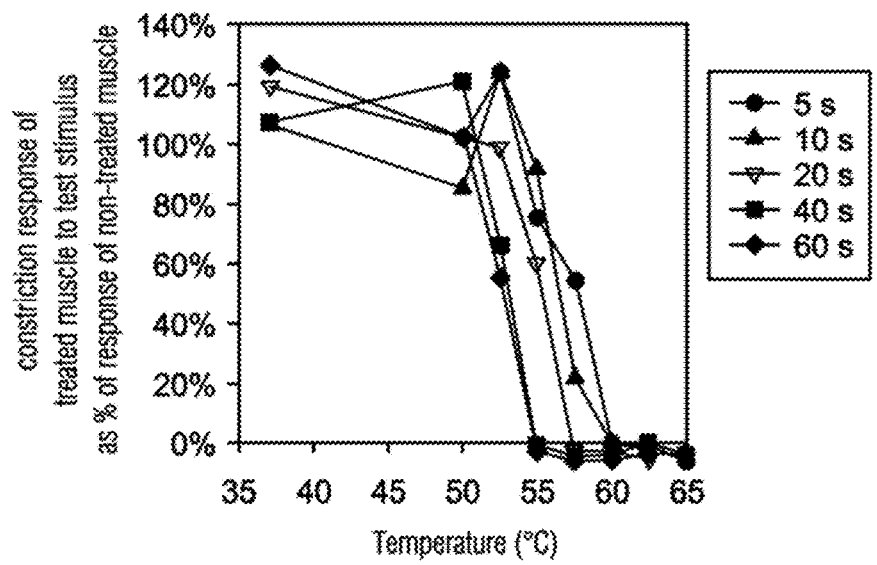
FIGS. 4A-B illustrate the effect of irradiation on the muscle response.
Figure 4B:
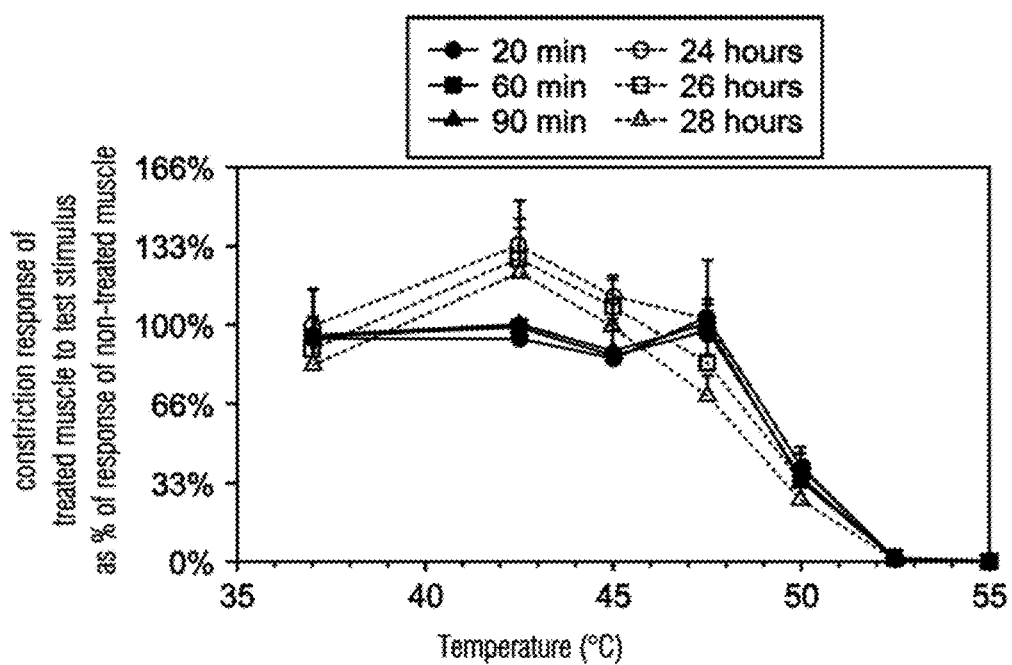

FIGS. 4A-B illustrate that heat treatments have been already studied and demonstrated to reduce muscle activity in human tissues, such as in the lung and the prostate, which have smooth muscle tissues similar to that of the iris. The heat treatment can reduce, or inhibit, muscle activity in these tissues. The duration of inactivity can last for hours to days in these systems (see Am. J. Respir. Cell Mol. Biol. Vol 44. pp 213-221, 2011). FIG. 4A illustrates the effect of heat treatments on lung smooth muscle. The muscle tissue was heated for a treatment time between 5 s and 60 s. After the heat treatment, a test stimulus was administered to the heat-treated and the untreated muscles. The graph reports the ratio of responses to this test as a function of the treatment temperature of the tissue. Visibly, as the treatment temperature exceeded 50 Celsius, or Centigrade, the response of the treated muscle to the test stimulus gradually decreased. For heat treatments above 55-60 Celsius, the response became negligible: the muscle was deactivated by the treatment.

FIG. 4B illustrates the same ratio of responses of treated muscles to non-treated muscles, with the difference that it indicates how long the effect lasted. As the curves show, the de-activation of the smooth muscle with heat treatments raising the muscle temperature above 50-55 Celsius lasted at least for 28 hours, and possibly longer. This remarkably long-lasting deactivation of smooth muscle in response to such a mild and short temperature increase is utilized by embodiments described in this document.

FIG. 5A illustrates an ophthalmic stimulator 100 for temporarily constricting a pupil 13 of an eye 1, building on the just-described observations, comprising an irradiation control system 110, to generate an irradiation control signal; art irradiation source 120, coupled to the irradiation control system 110, to generate an irradiation 200; and an irradiation delivery system 130, coupled to the irradiation control system 110, to receive the irradiation 200 from the irradiation source 120, and to deliver a patterned irradiation 200p to an iris 11 of the eye 1 in a pattern 210. In embodiments, the irradiation control system 110 controls at least one of the irradiation source 120 and the irradiation delivery system 130 with the irradiation control signal so that the patterned irradiation 200p causes a temporary constriction of the pupil 13 of the eye 1, without causing a permanent constriction of the pupil 13.

In some embodiments of the ophthalmic stimulator 100, the irradiation source 120 can include an incoherent light source, such as a light source, a LED, a lamp, an infrared source, a broad-band source, a narrow-band source, a radio-frequency source, an electromagnetic radiation source, or a sound source, to generate a light beam, an electromagnetic irradiation, an infrared beam, a LED light, or a sound. A separate class of irradiation sources can include a coherent light source, such as a laser, a pulsed laser, or a continuous wave (CW) laser.

The just discussed classes of incoherent and coherent irradiation sources have different advantages and drawbacks. Lasers offer good control and unparalleled precision. At the same time, laser beams have a very small diameter, often less than 100 microns. Therefore, to affect larger treatment regions, they require a complex and expensive, digitally controlled optical system, such as a scanning system. These laser-plus-scanning systems offer eat control and precision. At the same time, they can be expensive, and can introduce multiple sources of unreliability and performance degradation, a potential problem in medical applications, where high reliability is essential. Using lasers and scanners may therefore necessitate regular maintenance. Also, laser beams can be very intense, thus if a laser gets pointed to an unintended part of an ophthalmic tissue, it can cause substantial damage. Therefore, much stronger safety systems and precautions are needed in laser systems.

In contrast, non-coherent light sources, such as LEDs, infrared sources, lamps, infrared sources, and others may offer less precision and control. However, this control may be sufficient for the purposes of the here-described treatment. Also, incoherent light sources can make the ophthalmic stimulator 100 much simpler, lighter, and smaller at the same time. Since they typically do not require a digitally controlled scanning system, these incoherent light sources can also be cheaper to maintain and can be more robust and reliable. Finally, since these light sources are less intense, systems with incoherent light sources may require less stringent safety systems and measures. All in all, a comparative analysis of the competing advantages and disadvantages is performed when a system designer decides whether to use a coherent, or an incoherent light source as the irradiation source 120 of the ophthalmic stimulator 100.

Embodiments of the ophthalmic stimulator 100 can be characterized by numerous treatment parameters. These treatment parameters can include the followings. A power density of the patterned irradiation 200p of the irradiation delivery system 130 can be in the range of 0.1-1000 mW/cm$^2$, in some designs in the range of 1-100 mW/cm$^2$. A total power delivered by the patterned irradiation 200p to the iris can be in the range of: 0.1-1,000 mW, in some designs in the range of 1-100 mW. A total energy, deposited by the patterned irradiation 200p during the treatment can be in the range of 10 microJ-10 J, in some designs in the range of 100 microJ-100 mJ.

A wavelength of the irradiation source 120 can be in the range of 400-4,000 nm, in some designs, in the range of 600-1,500 nm. The wavelength of some stimulators 100 can be selected by noting in FIG. 2B, that the dilator muscle fibers 30 are located in the proximity of the pigmented epithelium of the iris 11. This fact can be used to selectively target and heat the dilator muscles 30 indirectly. The pigmented epithelium layers may not have essential functions that would be negatively affected by heating, such as undergoing an irrecoverable reactivity change. To build on this, irradiation sources 120 can emit the irradiation 200 with a wavelength close to the wavelength where the absorption of the pigmented epithelium shows a maximum, or is at least greatly enhanced. Such irradiation sources 120 can heat the pigments particularly efficiently, possibly to temperatures 55 C, 60 C, possibly even to 60-65 Celsius. The heated pigmented epithelia can then provide a secondary, or indirect heating to the dilator muscles 30, located in their immediate proximity, to the medically preferred 50-55 Celsius temperatures.

FIG. 2B also illustrates that the dilator muscles 30 are in the distal region of the iris 11. Therefore, irradiation with wavelengths that penetrate the iris tissue more efficiently and to greater depths can be favored to make sure that the dilator muscles 30 are well heated, in several ophthalmologic studies, irradiation with longer wavelengths showed greater penetration into ophthalmic tissues. Therefore, some irradiation sources 120 may emit irradiation 200 with longer wavelengths to penetrate more deeply into the iris, with eventual absorption by the pigmented epithelium, to achieve secondary heating of the dilator muscle fibers 30. Accordingly, a depth of a treated tissue within the iris can be in some designs in the range of 10 microns-3,000 microns, in some designs, in the range of 500-2,000 microns.

Some irradiation sources may emit a continuous, or continuous wave (CW) irradiation 200. Others, such as lasers, or LEDs, may emit pulsed irradiation. A frequency of the pulsed irradiation 200 can be, in a range of 1 Hz to 1 MHz, in some designs, in the range of 100 Hz to 100 kHz. The length of the emitted, pulses can vary from 10 femtoseconds to 1 second, in some designs from 1 microsecond to 1 millisecond. The total treatment time can be in the range of 1 sec to 300 sec, in some embodiments in the range of 10 sec to 100 sec. A beam profile of the patterned irradiation 200p can be a rectangular, a flat top, a smoothed, a Gaussian, or a Lorentzian profile.

An inner radius Rp(inner) of the pattern 210 can be in the range of 2-10 mm, in some designs in the range of 3-6 mm. An outer radius Rp(outer) of the pattern 210 can be in the range of 3-15 mm, in some designs, in the range of 5-10 mm. The pattern 210 can be such that a treated fraction of the iris has an area that is 10-80% of the total area of the iris 11, in some design, this fraction can in the range of 20-50%.

In some embodiments, the irradiation delivery system 130 can include a pattern generator, an optical beam shaper, a patterning optics, a beam profiler, or a digitally controlled irradiation optics. Some of these elements can be built mostly from passive optical elements, such as lenses and mirrors, with some system characteristics controlled electronically, such as a telescopic distance between two lenses. In other embodiments, the irradiation delivery system 130 can include optical elements that are actively operated and controlled by electronic or digital circuitry, as described below.

Some embodiments of the ophthalmic stimulator 100 can be configured to increase a temperature of a treatment region of the iris to a range of 45-60 degrees Celsius. Other embodiments can increase the temperature of the treatment region of the iris to a range of 50-55 degrees Celsius. As discussed in relation to FIGS. 4A-11, treatments with temperatures in these ranges have been demonstrated to impact the responsiveness of smooth muscle tissue temporarily, in a reversible and repeatable manner.

The actual effect of the heat treatment depends on several factors, since different temperatures and treatment durations can have a multitude of effects on smooth muscle cells and function. On the cellular level, first, a heat treatment can induce biochemical changes and secretions that can affect the functioning of the treated tissue, such as heat shock proteins. Second, it can cause loss of cells through various mechanisms, such as apoptosis, or programmed cell death. Finally, on a much shorter time scale, heat treatment can lead to specific loss of contractility due to denaturation of myosin molecules or inhibition of ion channels.

On a higher, physiological level, the effect of the heat treatment on the pupil may depend on factors such as dilator muscle fiber, orientation, and on opposing, constrictor, muscle action. Finally, the heat treatment can change the physical properties of the muscles in different aspects as well, including shrinking or expanding the length of the muscle strands, making the strands more or less aligned, and changing of the elastic moduli of the muscles, among others.

For all these reasons, the iris of the individual patients can be analyzed by the ophthalmologist before the treatment with the ophthalmic stimulator 100. Based on the analysis, the desired medical outcomes can be cross-referenced with the patient data of the individual patients. Subsequently, the treatment region, treatment parameters and specifically the treatment temperatures can be set. As discussed further below, for some medical outcomes heating the radial dilator muscles 30 can be preferable, for others, heating the circular sphincter muscles 40 can be preferable. The treatment regions can be set according to these medical considerations.

FIGS. 6A-D illustrate that in some embodiments of the ophthalmic stimulator 100, the irradiation control system 110 can include an irradiation controller 112, an imaging system 114 and a user interface 118. The imaging system 114 can be electronically coupled to the irradiation controller 112, to relay images, image-related data, and control information.

Figure 6A:
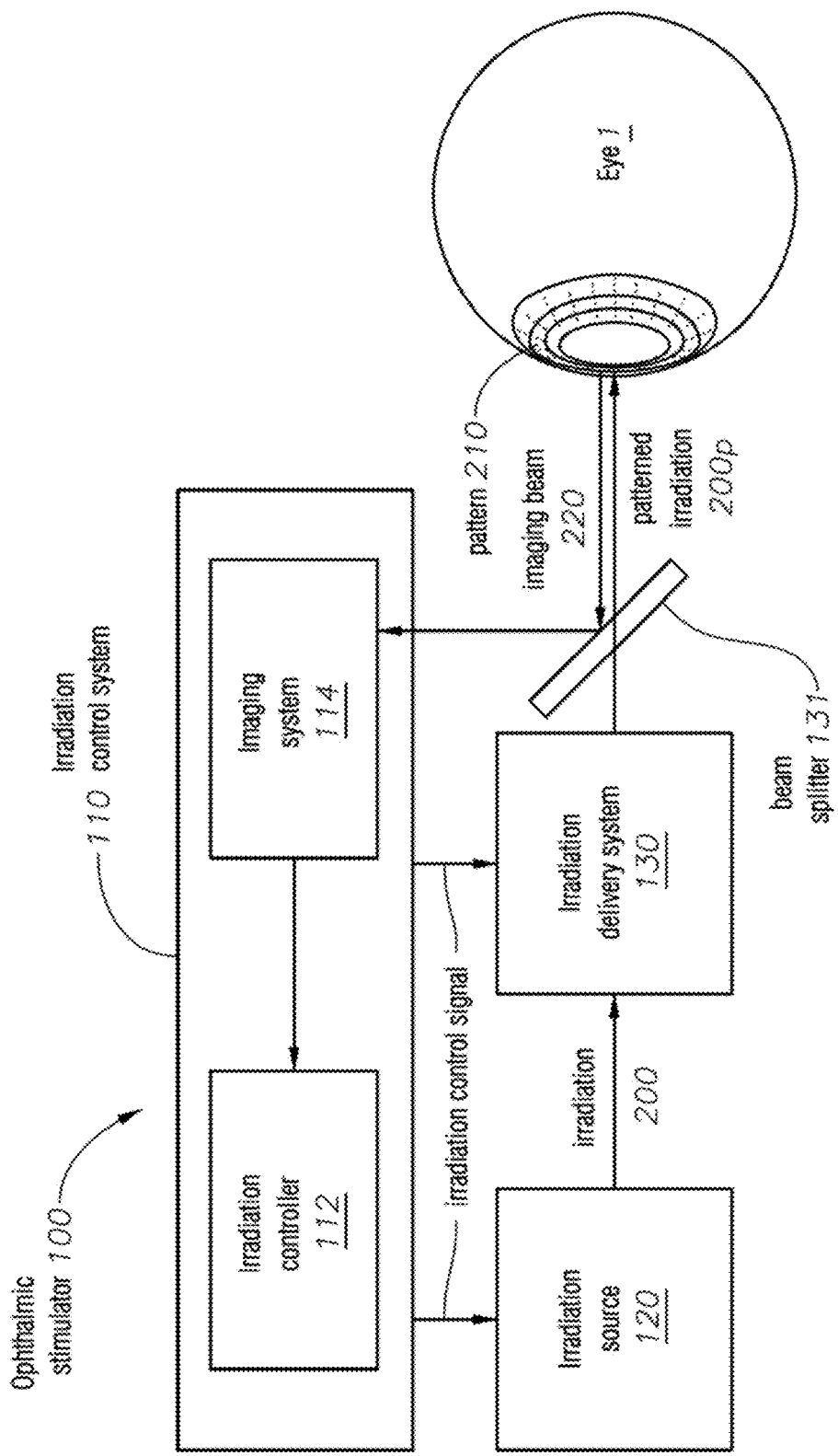
Figure 6B:
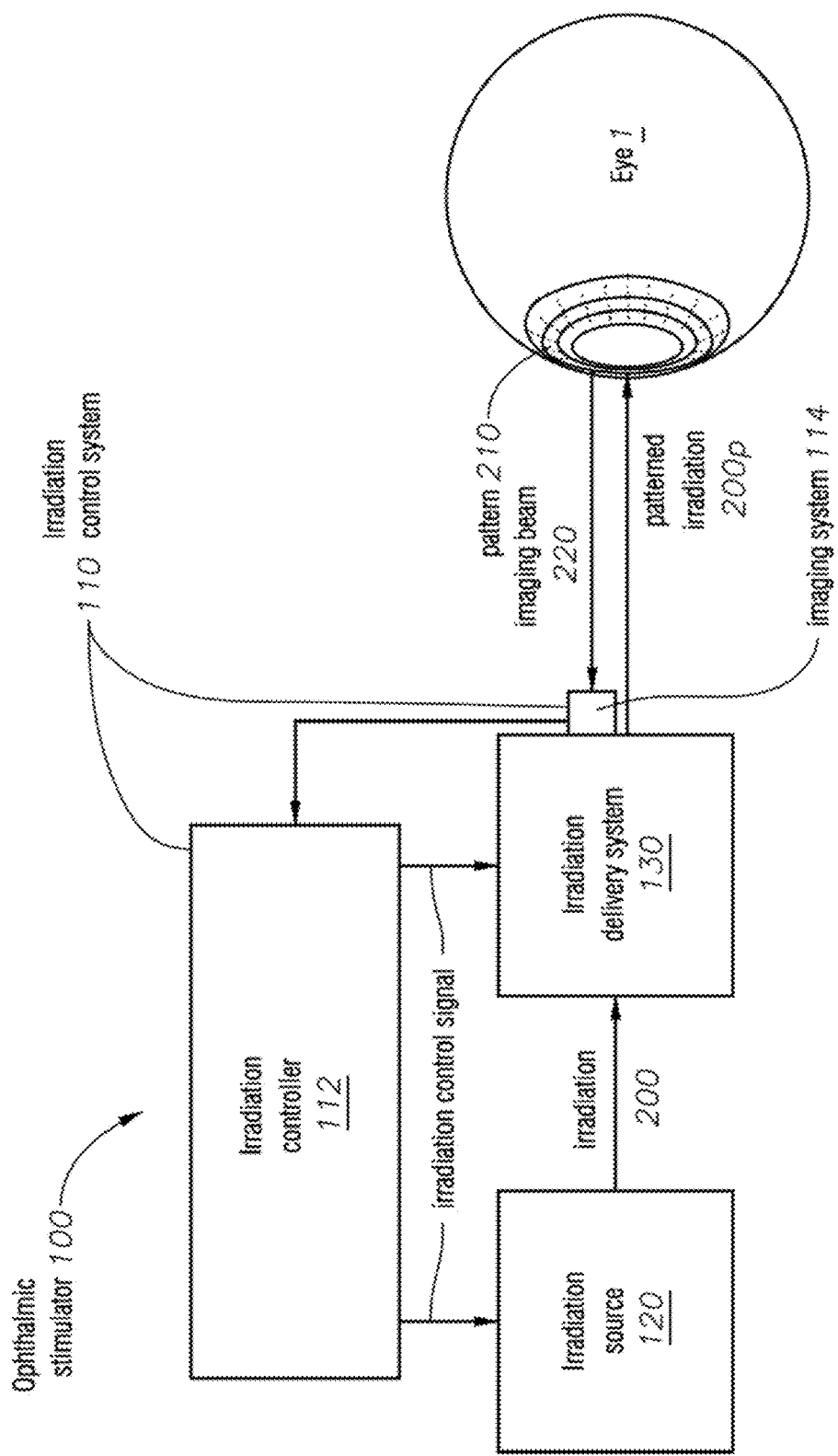

FIGS. 6A-B illustrate two implementations of the imaging system 114. In FIG. 6A, an imaging beam 220 is reflected out from the optical pathway of the patterned irradiation 200p by a beam splitter 131 towards the imaging system 114 that is positioned outside the irradiation optical pathway. In FIG. 6B, a small imaging system, such as a small CCD camera 114 can be placed on the distal end of the irradiation delivery system 130, directly receiving the imaging beam 220. The imaging beam 220 can be a reflection of an imaging light, projected on the iris 11 by an imaging light source. In other designs, the imaging beam 220 can be simply the ambient light reflected from the iris 11.

The imaging system 114 can be any one of the well known ophthalmic imaging systems, including a CCD camera, feeding into a video monitor, any other electronic or digital imaging system, a video microscope, or a surgical microscope.

The irradiation control system 110 can generate the irradiation control signal by generating an image of the iris 11 of the eye with the imaging system 114 for a user, followed by receiving an image-based input from the user through the user interface 118, and generating the irradiation control signal to control the irradiation delivery system 130 to deliver the patterned irradiation 200p in accordance with the received image-based input.

In a typical example, the patterned irradiation 200p can impact the iris 11 in a ring pattern 210 with an inner radius Rp(inner) and an outer radius Rp(outer). In this embodiment, the user of the system, such as ophthalmologist, or an ophthalmic surgeon, can be prompted via the user interface 118 to enter the image-based input, which in this case can be a selection of the inner radius Rp(inner) and the outer radius Rp(outer) of the ring pattern 210, based on the surgeon analyzing the image, relayed by the imaging system 114.

Figure 12A:
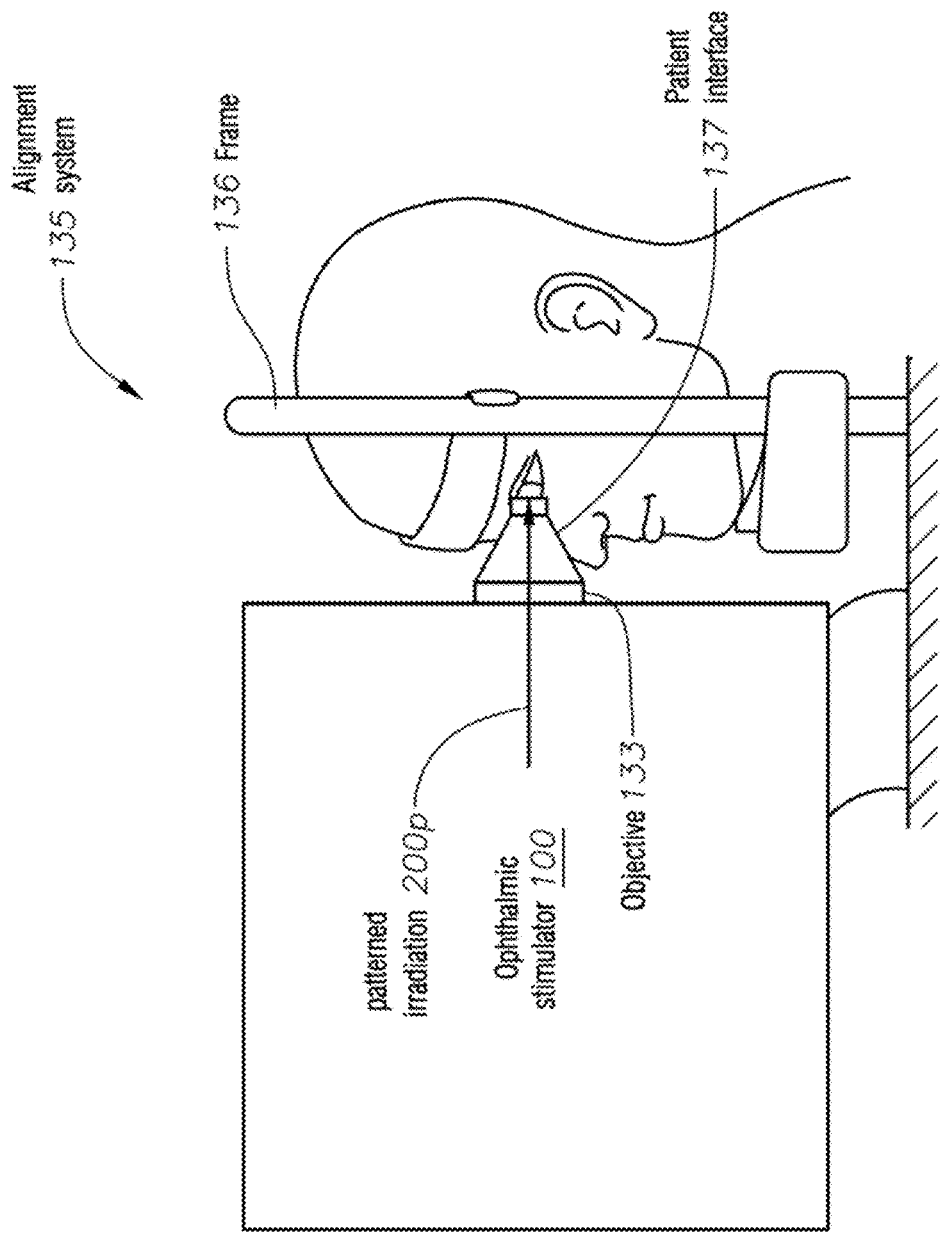
FIGS. 12A-E illustrate embodiments of the alignment system 135.
Figure 12B:
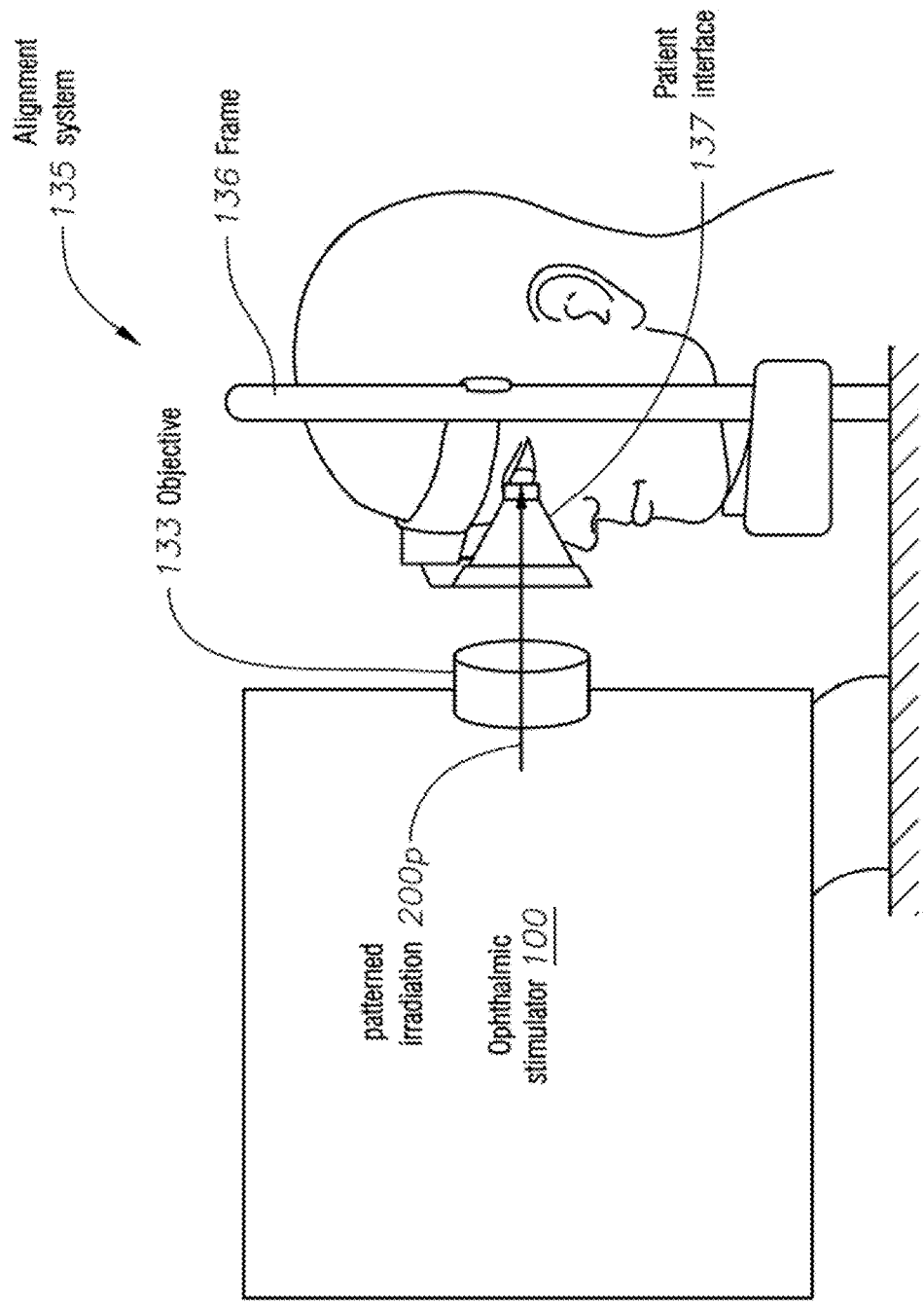
Figure 12C:
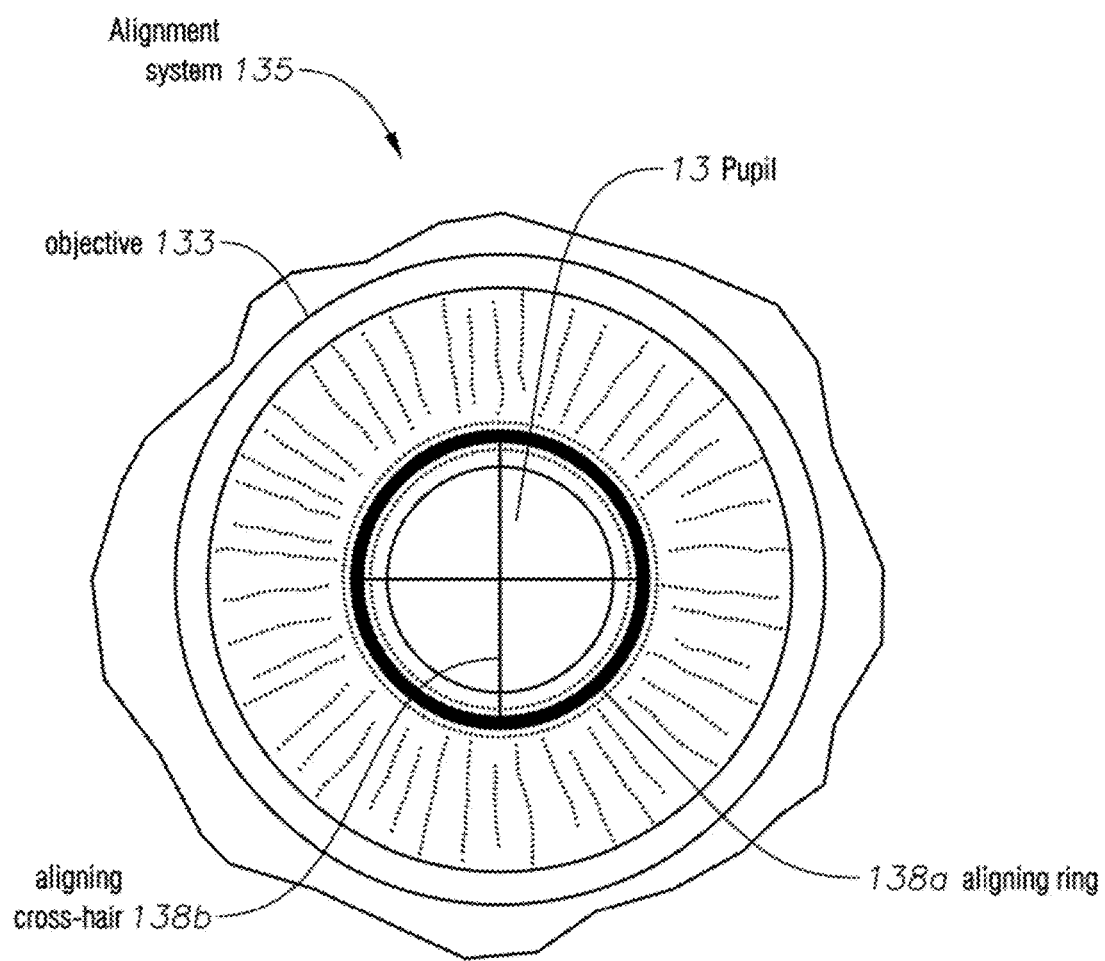
Figure 12D:
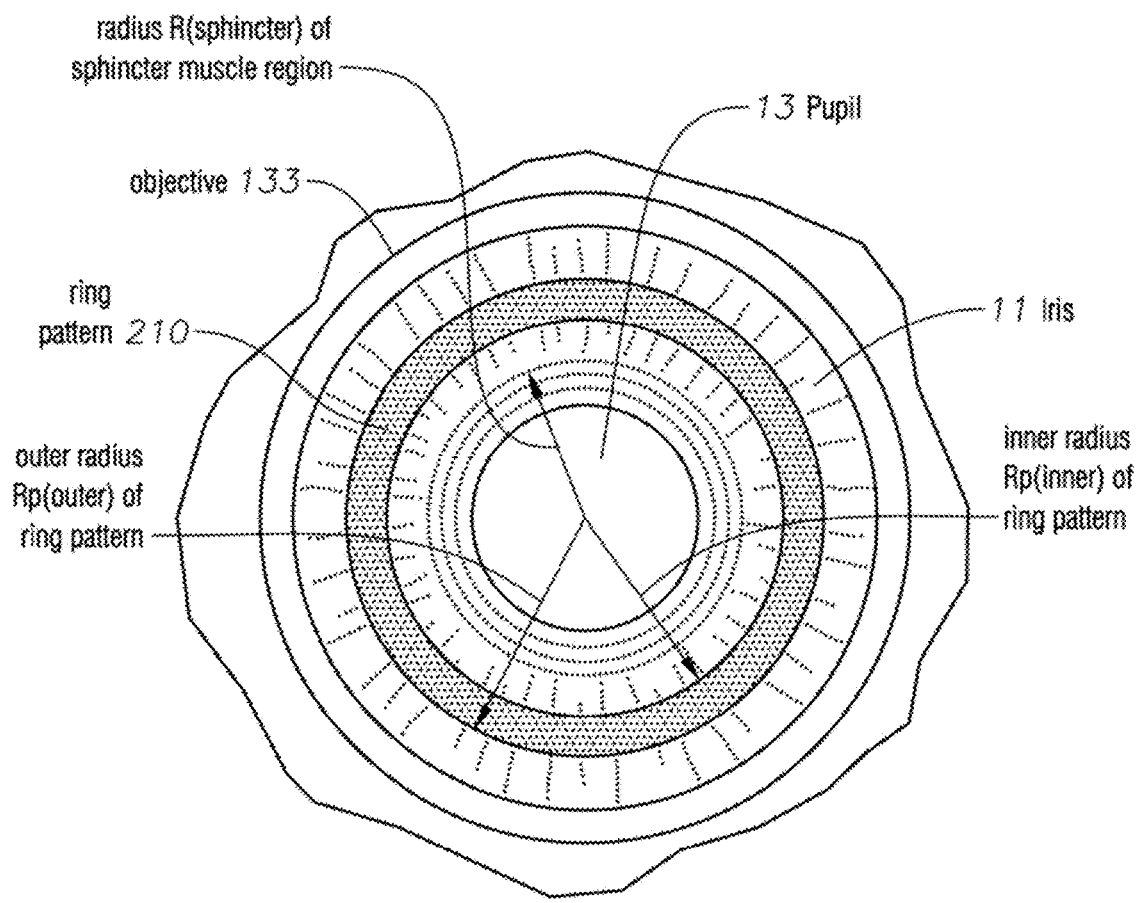
Figure 12E:
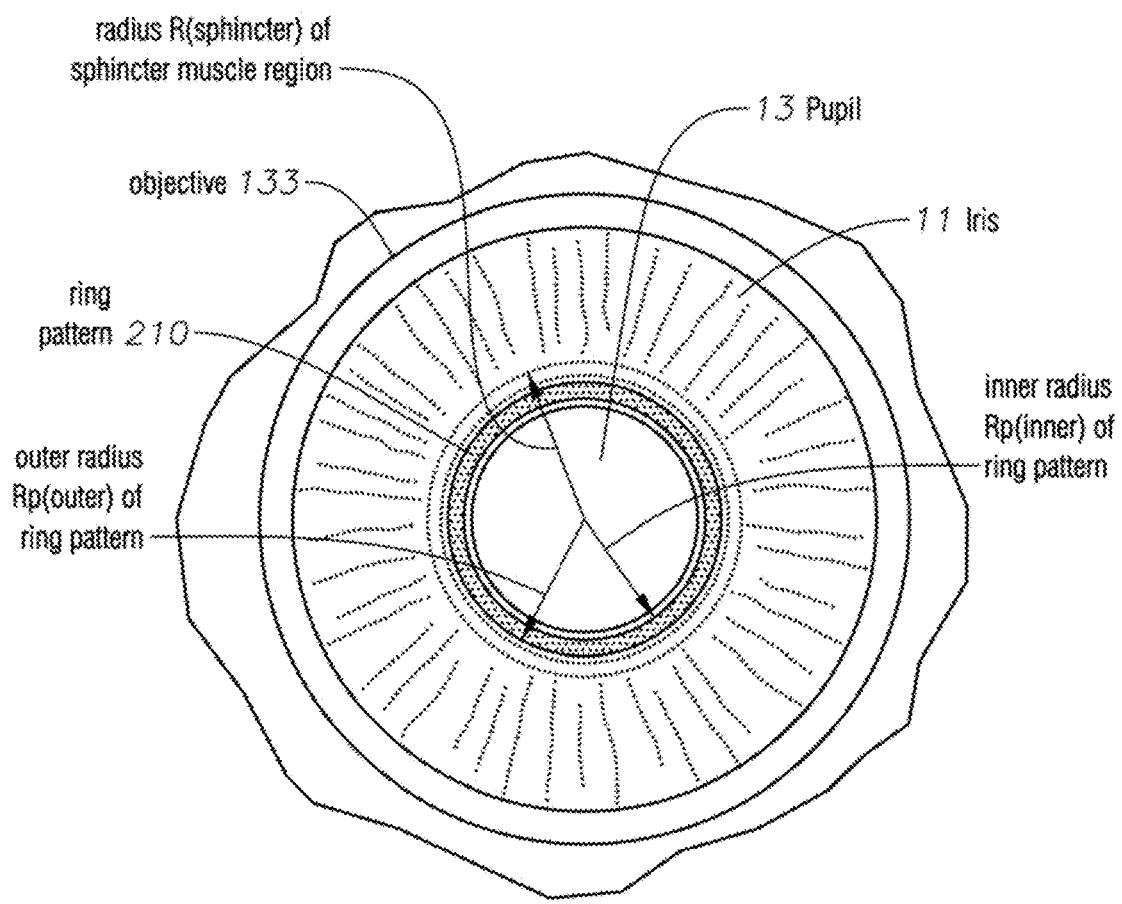
Figure 13A:
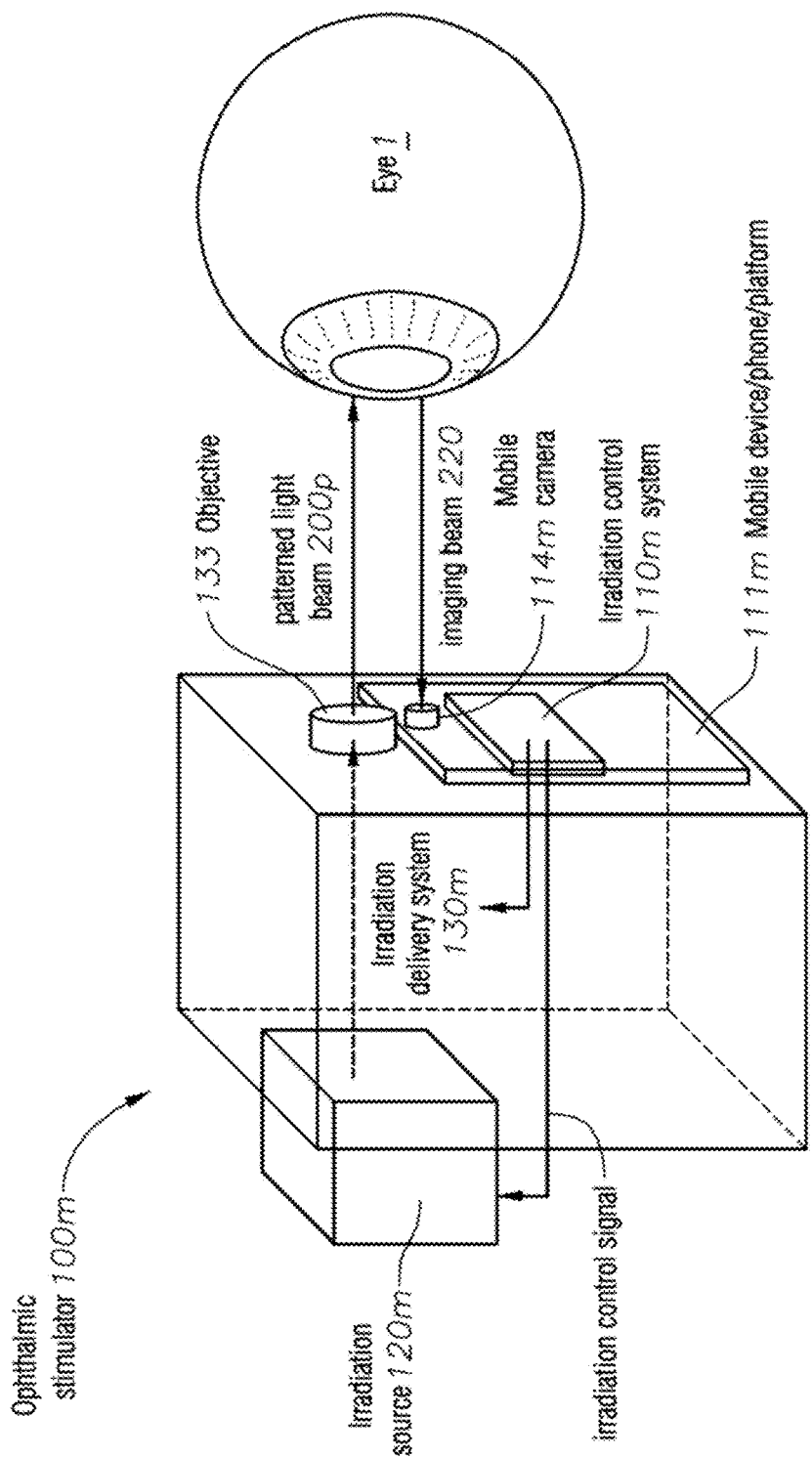
Figure 14:
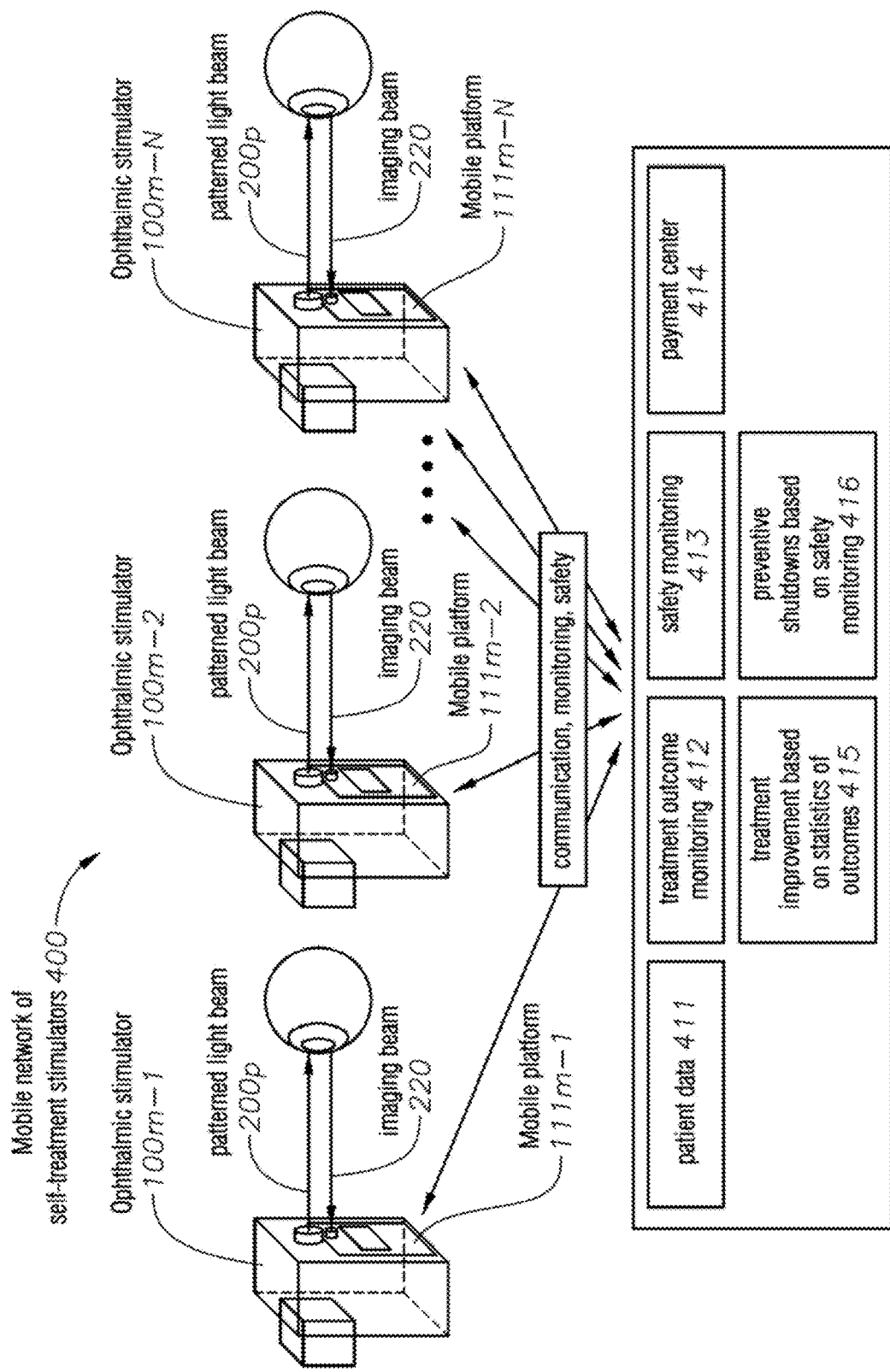
FIG. 14 illustrates a mobile network of self-treatment stimulators 400.
Figure 15:
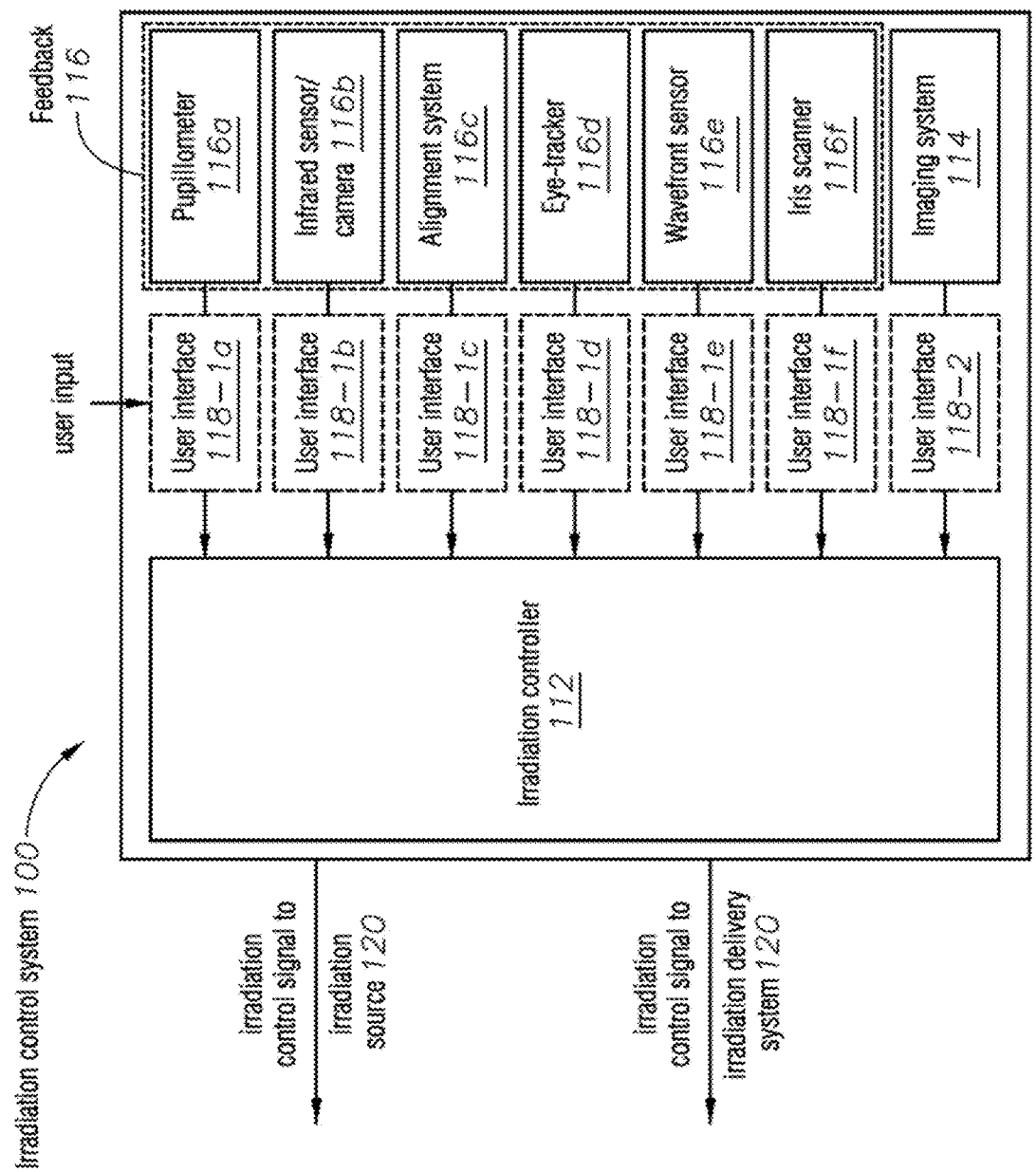
FIG. 15 illustrates an embodiment of the feedback system 116.
Figure 16A:
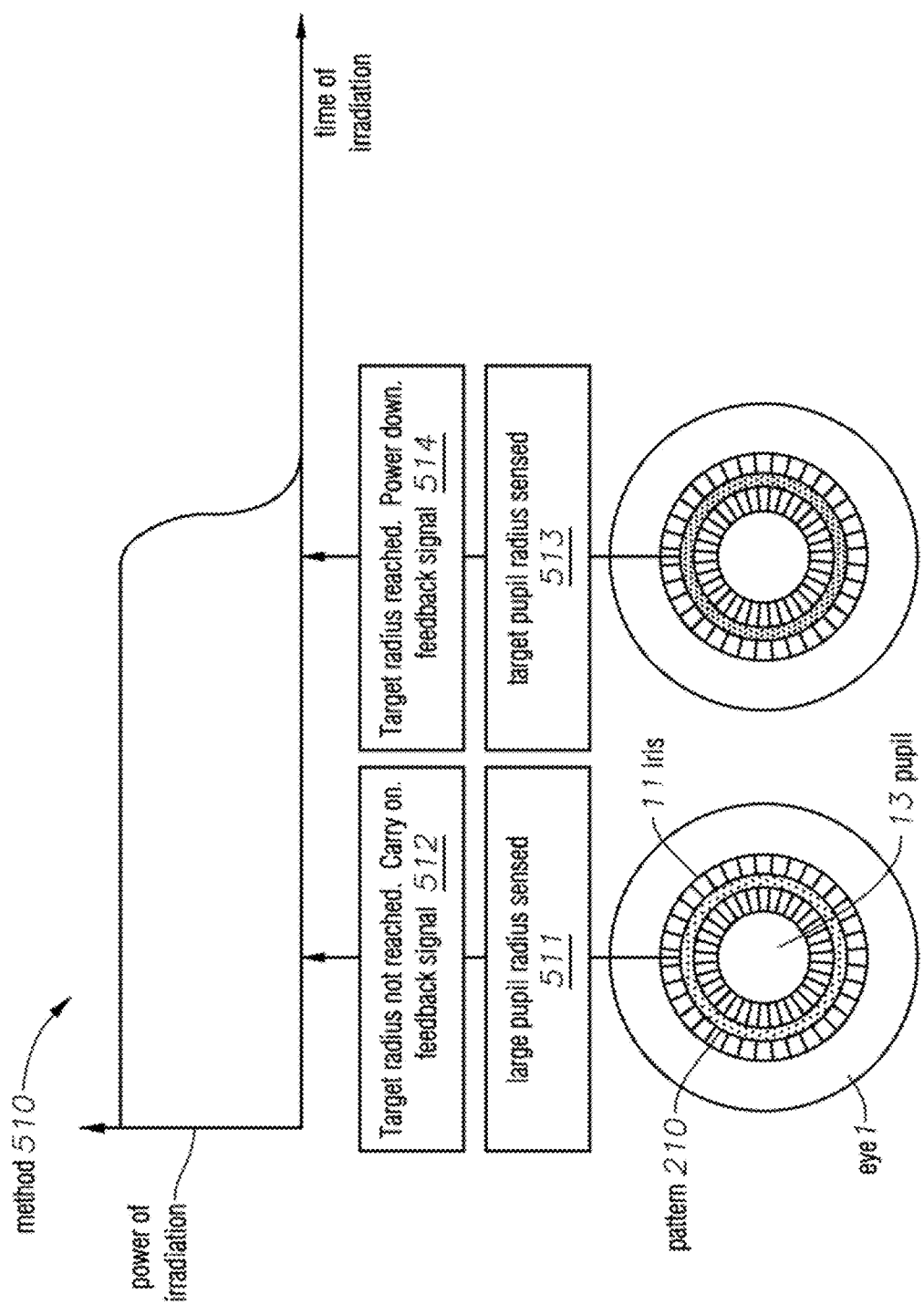
FIGS. 16A-E illustrate methods 510-550.
Figure 16B:
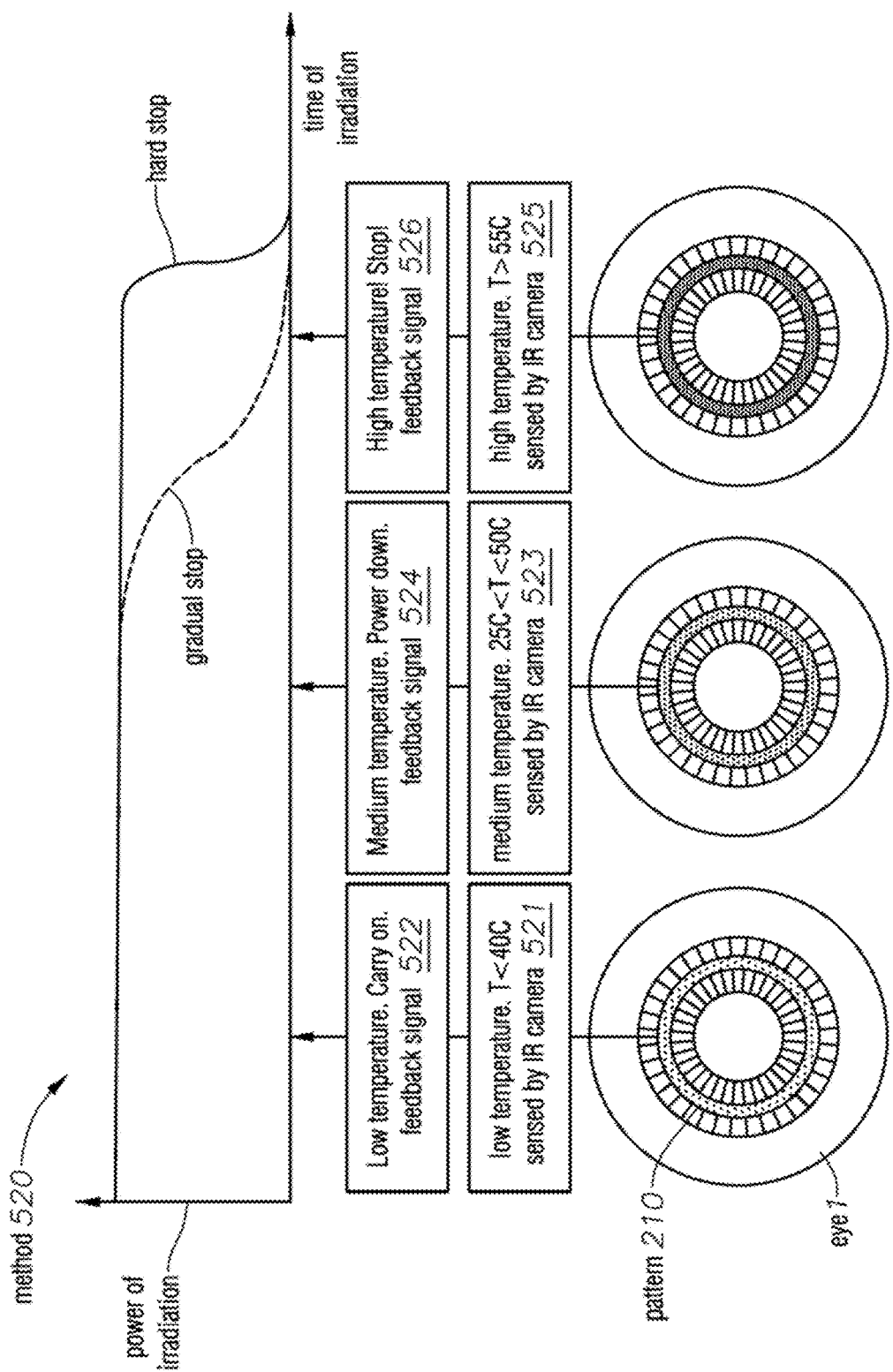
Figure 16C:
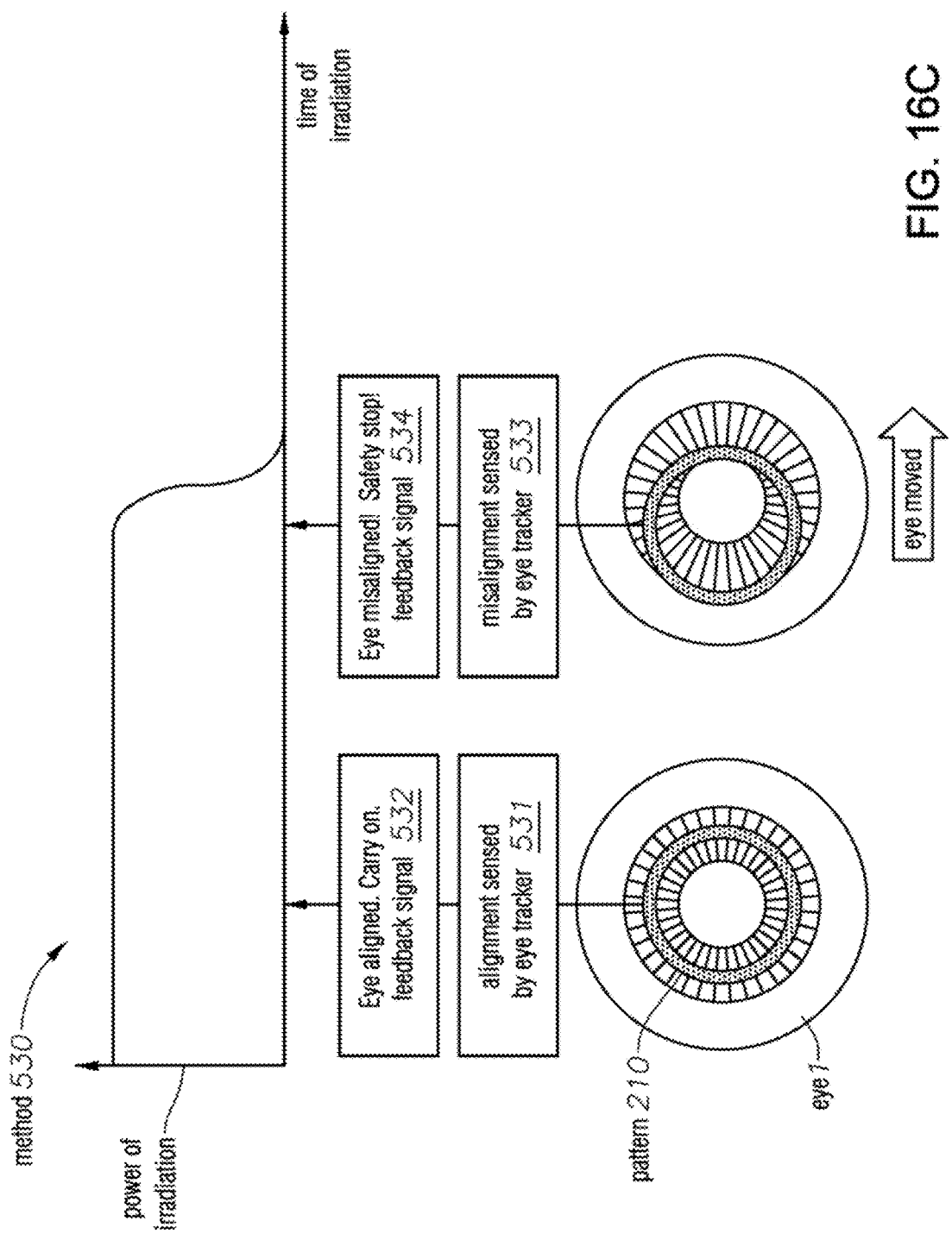
Figure 16D:
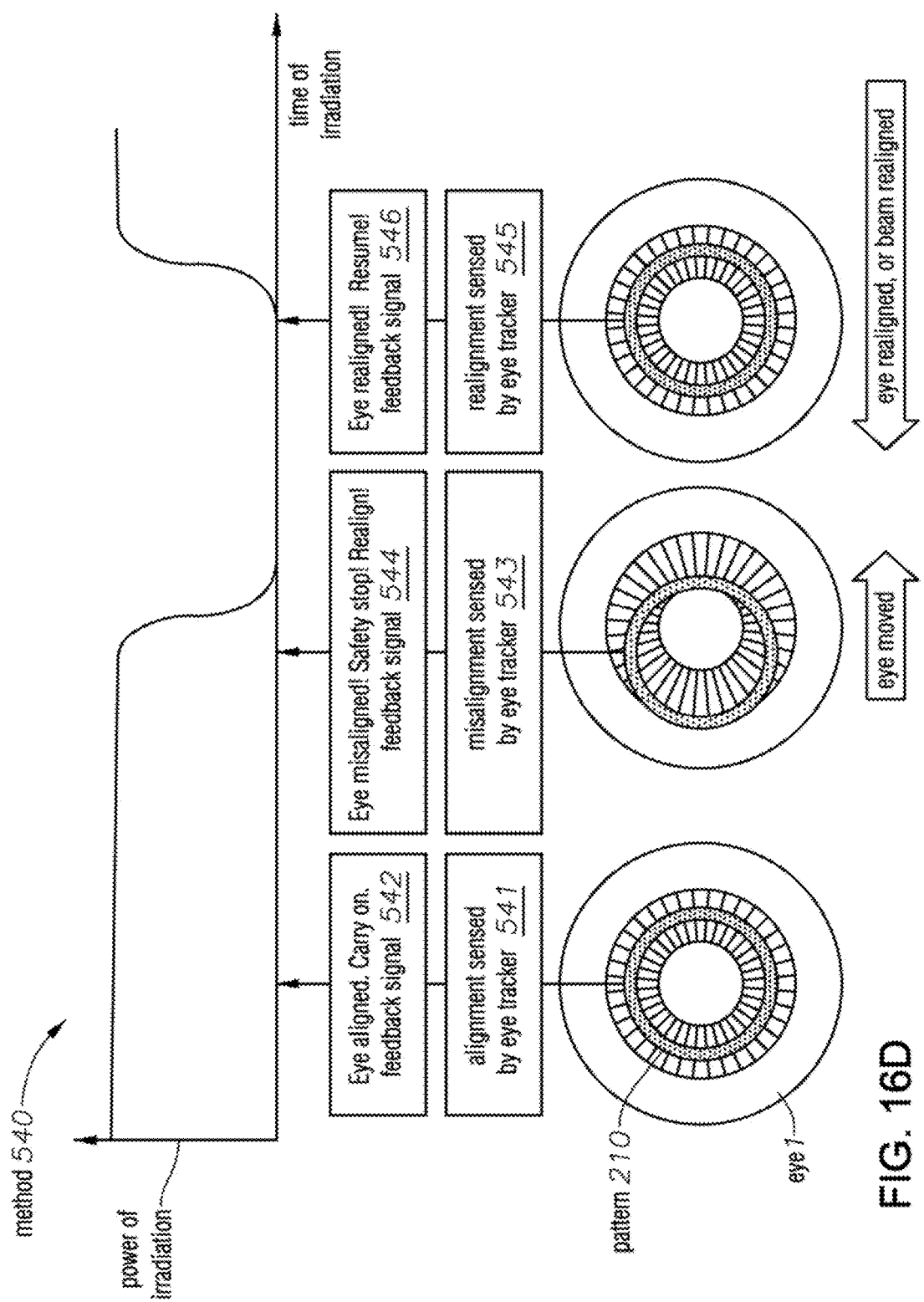
Figure 16E:
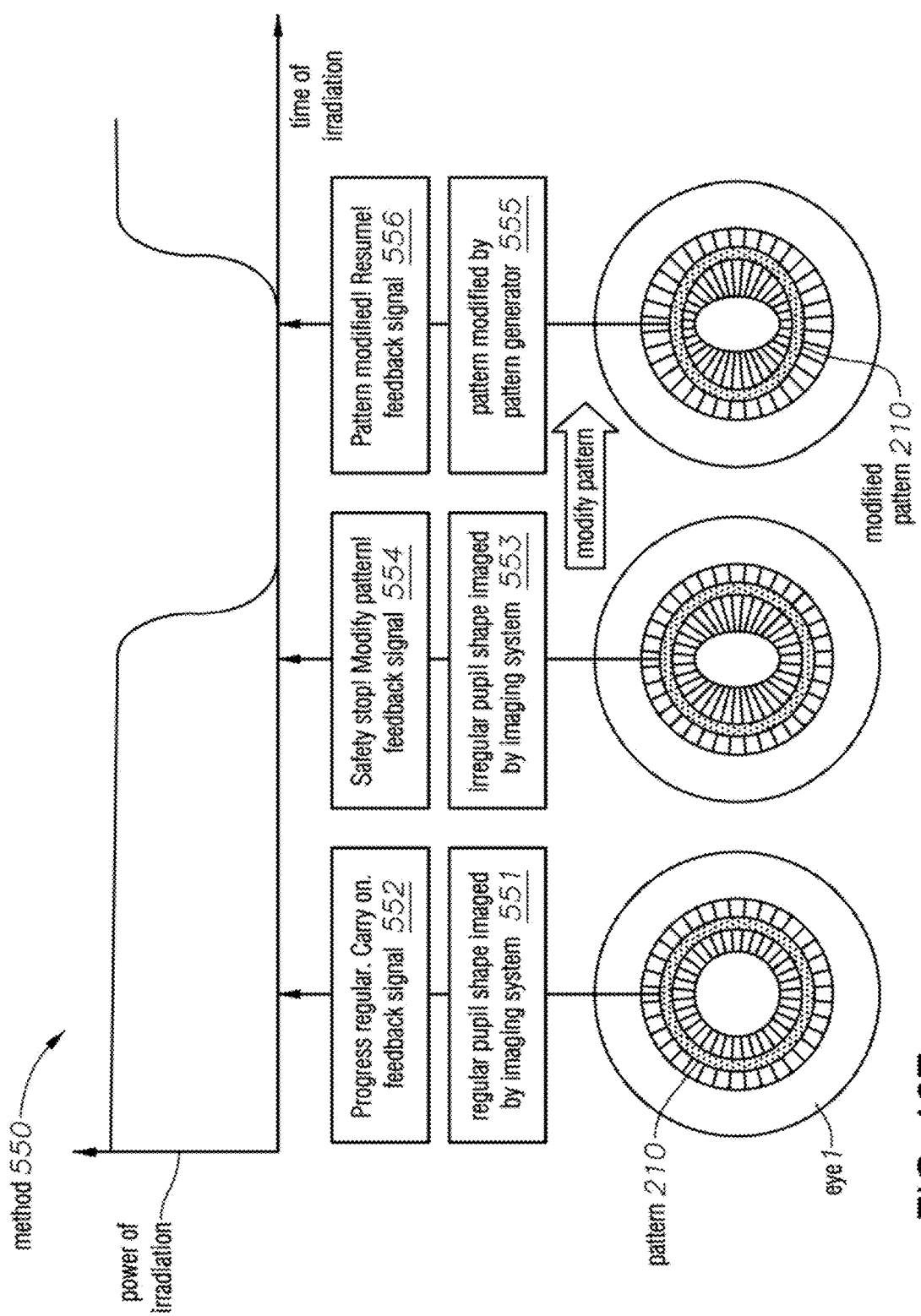
Figure 17B:
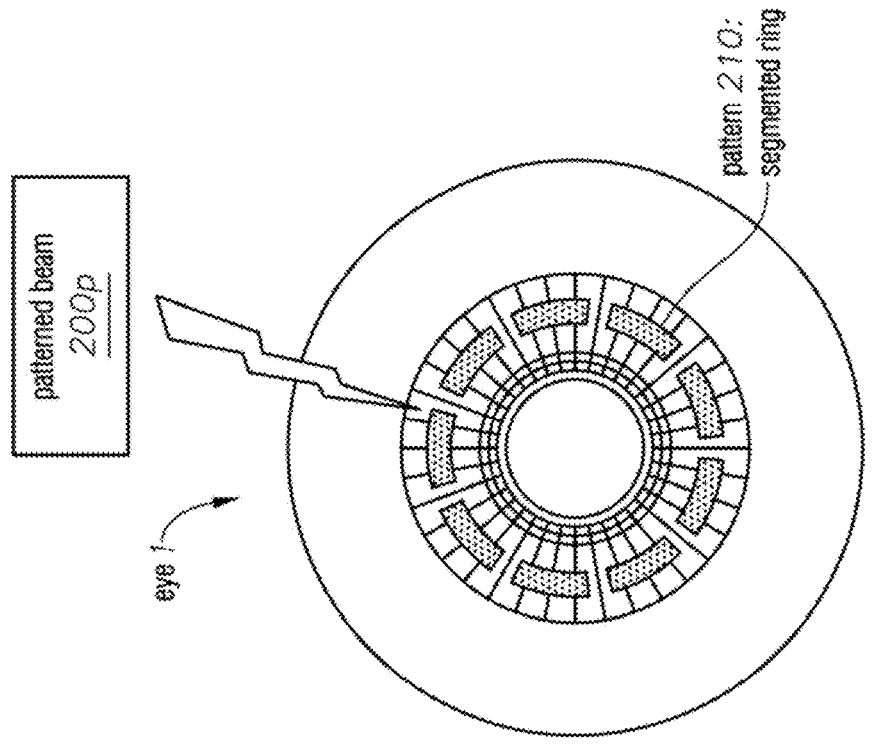
FIGS. 17A-D illustrate various irradiation patterns 210.
Figure 17A:
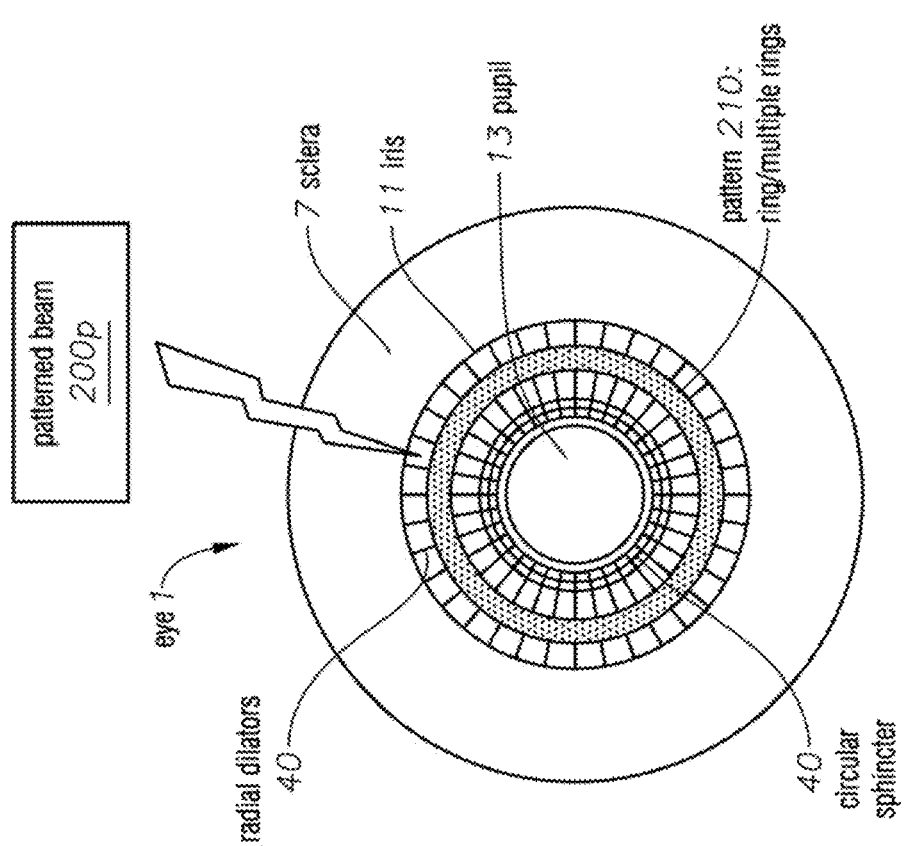
Figure 17D:
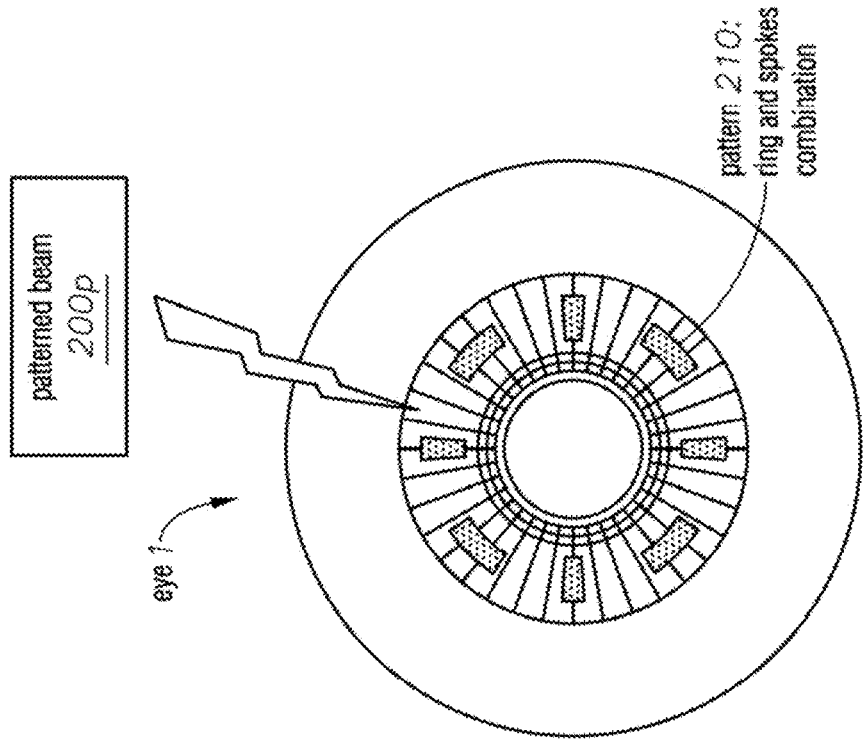
Figure 17C:
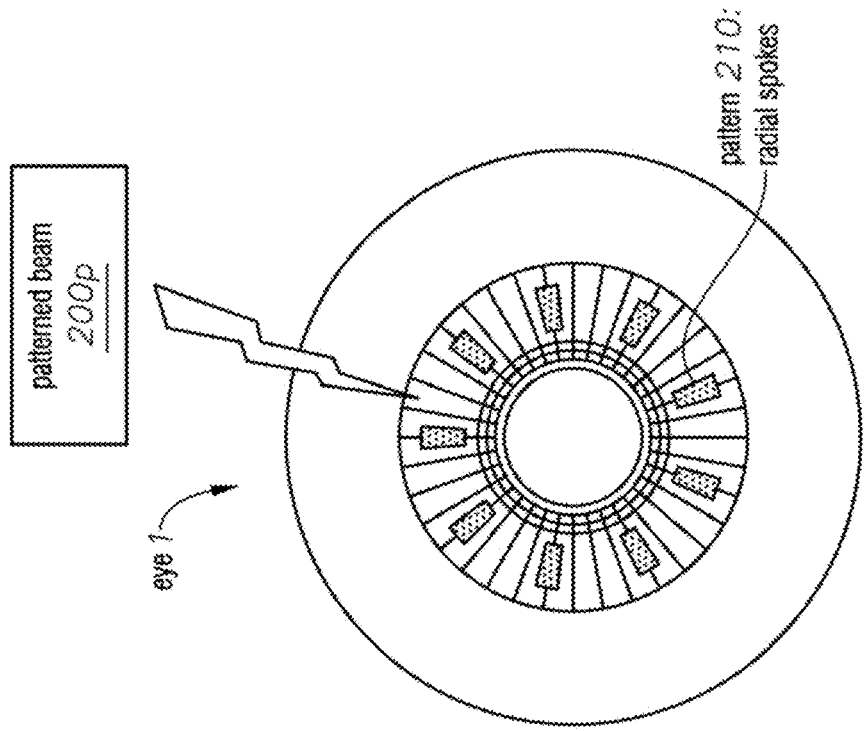

FIGS. 12D-E illustrate that setting these radii Rp(inner) and Rp(outer) determines whether the ring pattern 210, and thus the treatment region, is the region of the radial dilator muscles 30, or the circular sphincter muscles 40. Denoting the outer radius of the sphincter muscles with R(sphincter), if the surgeon selects the inner radius Rp(inner) of the ring pattern 210 to be greater than R(sphincter): Rp(inner)>R (sphincter), then the ring pattern 210 will fall on the radial dilator muscles 30, and those muscles will receive the heat treatment. Whereas, if the surgeon selects the outer radius Rp(outer) of the ring pattern 210 to be smaller than R(sphincter): Rp(outer)<R(sphincter), then the ring pattern 210 will fall on the circular sphincter muscles 40, and the circular sphincter muscles 40 will be treated by the patterned irradiation 200p. As discussed, an ophthalmologist can select either treatment region based on a prior analysis of the patient's specific data, and the desired medical outcomes.

In some embodiments, the irradiation control system 110 can include an image processor 114ip in the imaging system 114. The image processor 114ip can be integrated with the imaging system 114, can be partially integrated, or can be a separate electronic or computational system, in these embodiments, the irradiation control system 110 can generate the irradiation control signal by generating an image of the iris 11 with the imaging system 114 for the image processor 114ip, receiving an image-based input from the image processor 114ip, and generating the irradiation control signal to control the irradiation delivery system 130 to deliver the patterned irradiation 200p in accordance with the received image-based input.

In a representative embodiment, the patterned irradiation 200p can impact the iris 11 in a ring pattern 210 with inner and outer radii Rp(inner) and Rp(outer). The imaging system 114 can image the iris 11, and relay this image to the image processor 114ip. In response, the image processor 114ip can run an image recognition program, possibly including an edge-recognition software, and identify the inner and outer radii of the iris 11, and the radius R(sphincter) that demarcates the radial dilator muscles 30 from the circular sphincter muscles 40. Then, the image processor 114ip can generate the image-based input that sets, or suggests to set, the Rp(inner) and Rp(outer) radii of the ring pattern 210. The effect of these choices on the treatment region and the corresponding medical effects have been explained earlier.

FIG. 12A-C illustrate that in some embodiments of the ophthalmic stimulator 100, the irradiation control system 110 can include an alignment system 135.

FIG. 12A illustrates that in some embodiments the ophthalmic stimulator 100 can include an objective 133, the last optical element that guides the patterned irradiation 200p toward the eye 1. In these embodiments, the alignment system 135 can include a frame, or chin-rest 136, on which the patient can rest her/his chin to minimize the motion of the eye 1 relative to the stimulator 100. The alignment system 135 can also include a patient interface 137 that contacts the eye 1 of the patient. Many types of patient interfaces 137 are known in the art and can be used here. FIG. 12A illustrates a patient interface 137, whose proximal end is attached to the objective 133 of the ophthalmic stimulator 100, and whose distal end the patient presses her eyes against. The patient interface 137 can ensure a firm coupling, or docking, to the eye by involving a vacuum suction system, or a forceps. The patient interface 137 can be a one-piece or a two-piece patient interface. The distal end of the patient interface 137 can include a contact lens, to ensure a smoother, softer connection to the eye. Such a contact lens also minimizes the optical distortions of the patterned irradiation 200p as it exits the patient interface 137 and enters the cornea 5 of the eye 1.

FIG. 12B illustrates another embodiment of the alignment system 135, where the patient interface 137 is coupled to the frame 136 instead of the stimulator 100. Since the frame 136 is rigidly coupled to the ophthalmic stimulator 100, the optical pathway of the patterned light 200p is similarly secure from the objective to the eye 1 in this embodiment as well. One of the differences is that there is a distance between the stimulator 100 and the patient interface, 137, so the patient does not have to lean forward to receive the treatment, and the doctor sees where the patterned light 200p hits the patient interface 137. As before, this patient interface 137 can also be a one-piece and a two-piece patient interface 137.

The patient interfaces 137 of either FIG. 12A or 12B is preferably aligned and centered with the eye 1 before coupling, or docking them to the eye 1. FIG. 12C illustrates a corresponding aligning, or centering, pattern 138 of the alignment system 135. This centering pattern can include an aligning ring 138a, or an aligning cross-hair 138b, or both. This aligning pattern 138 can be formed in, projected into, or digitally overlaid, the image formed by the imaging system 114, in a position that is concentric with the optical axis of the objective 133. The ophthalmic surgeon, or any other user or operator, can dock the patient interface 137 of the stimulator 100 to the eye with increased precision, with aligning, or centering, the aligning element 138 with the pupil 13 during the docking procedure.

In a video-monitor-based embodiment, the surgeon can make the centering of the aligning ring 138a on the video image with the edge of the pupil 13 part of the docking. During the docking, the surgeon can instruct the patient to move her/his head and eye around, until the circular edge of the pupil 13 is concentric with the aligning ring 138a. Then the surgeon can complete the docking of the patient interface 137 to the eye 1.

In some designs, the stimulator 100 can include a fixation light 202, and the surgeon can instruct the patient to stare at the fixation light 202 during docking. The patient staring, or fixating at the fixation light 202 can further help centering the patient interface 137 with the pupil 13 during the docking.

In these embodiments, the irradiation control system 110 can generate the irradiation control signal by processing alignment data with the alignment system 135, and generating the irradiation control signal to control the irradiation delivery system 130 to deliver the patterned irradiation 200p to the iris in a pattern 210 aligned with the pupil 13 of the eye.

In some embodiments of the ophthalmic stimulator 100, the processing alignment data can include generating an image of the iris 11 with the imaging system 114, and overlaying an alignment pattern 138 on the generated image. The generating the irradiation control signal can include generating a misalignment-warning signal, or generating an alignment-guidance signal, if a misalignment is detected during the processing of the alignment data that is part of the docking. The misalignment-warning signal can alert the operating surgeon to instruct the patient to move his/her head, eye, or both to improve the alignment to help making the docking precise. Also, for stimulator designs where the stimulator 100 or the patient interface 137 itself can be moved or adjusted, the misalignment-warning signal can alert the surgeon for the need to adjust the stimulator 100 or the patient interface 137.

An example for an adjustable patient interface 137 is a two-piece patient interface 137, where one piece of the patient interface 137 can be attached to the stimulator 100 at its objective 133, the other piece of the patient interface 137 can be coupled to the eye with vacuum-suction, or pressing, and the docking includes the surgeon maneuvering the two pieces of the patient interface 137 to dock to each other.

Figure 6D:
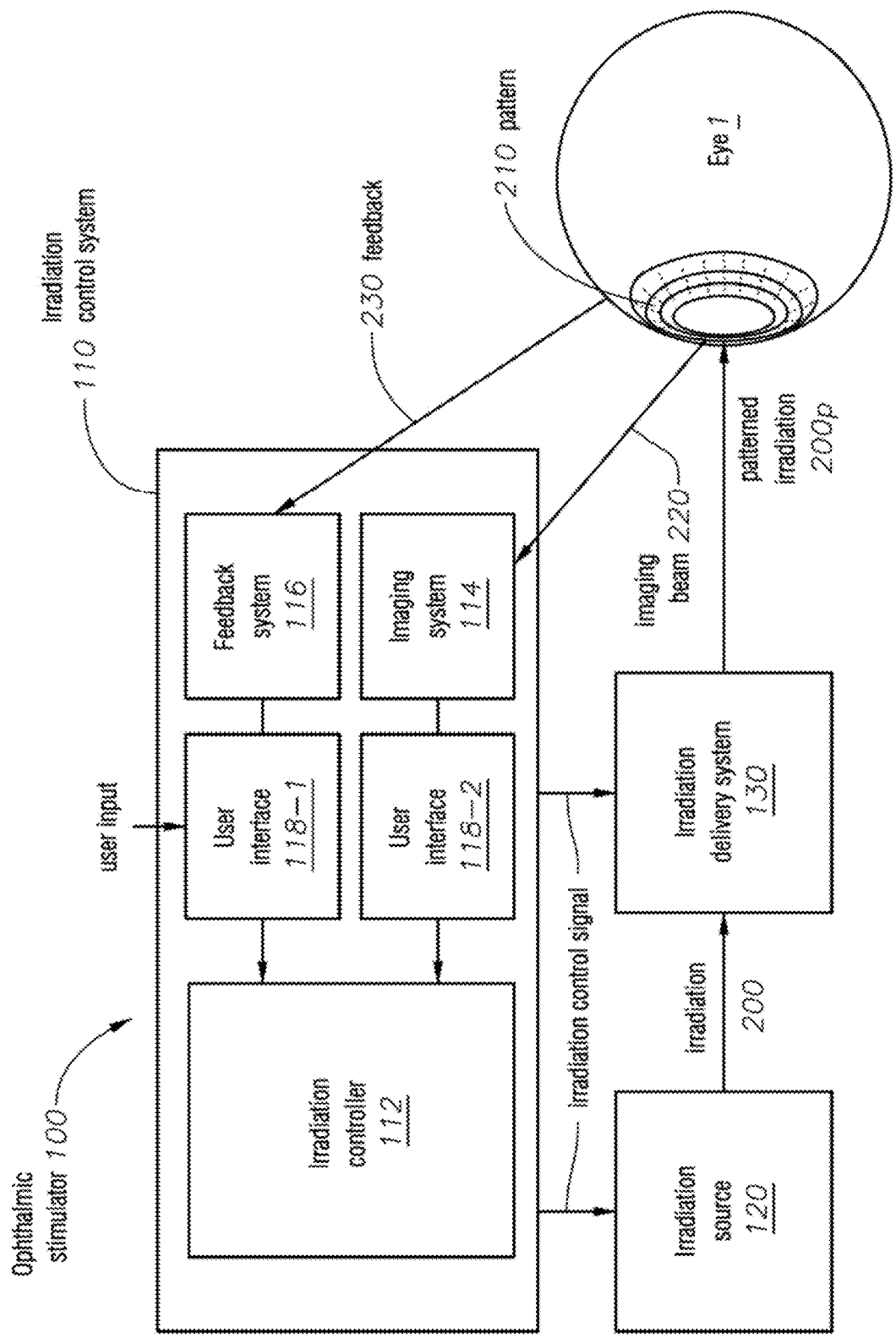
Figure 7A:
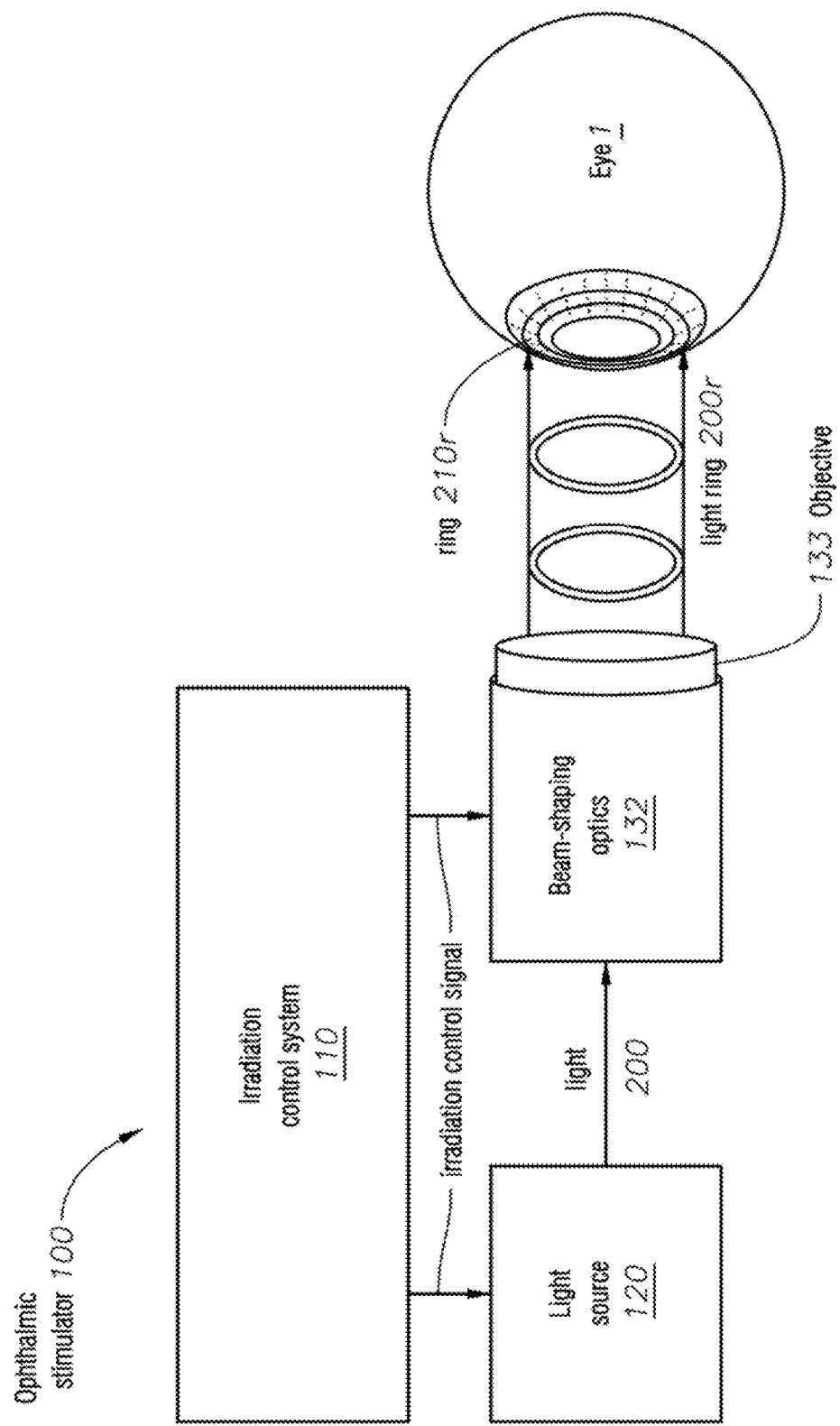
Figure 7B:
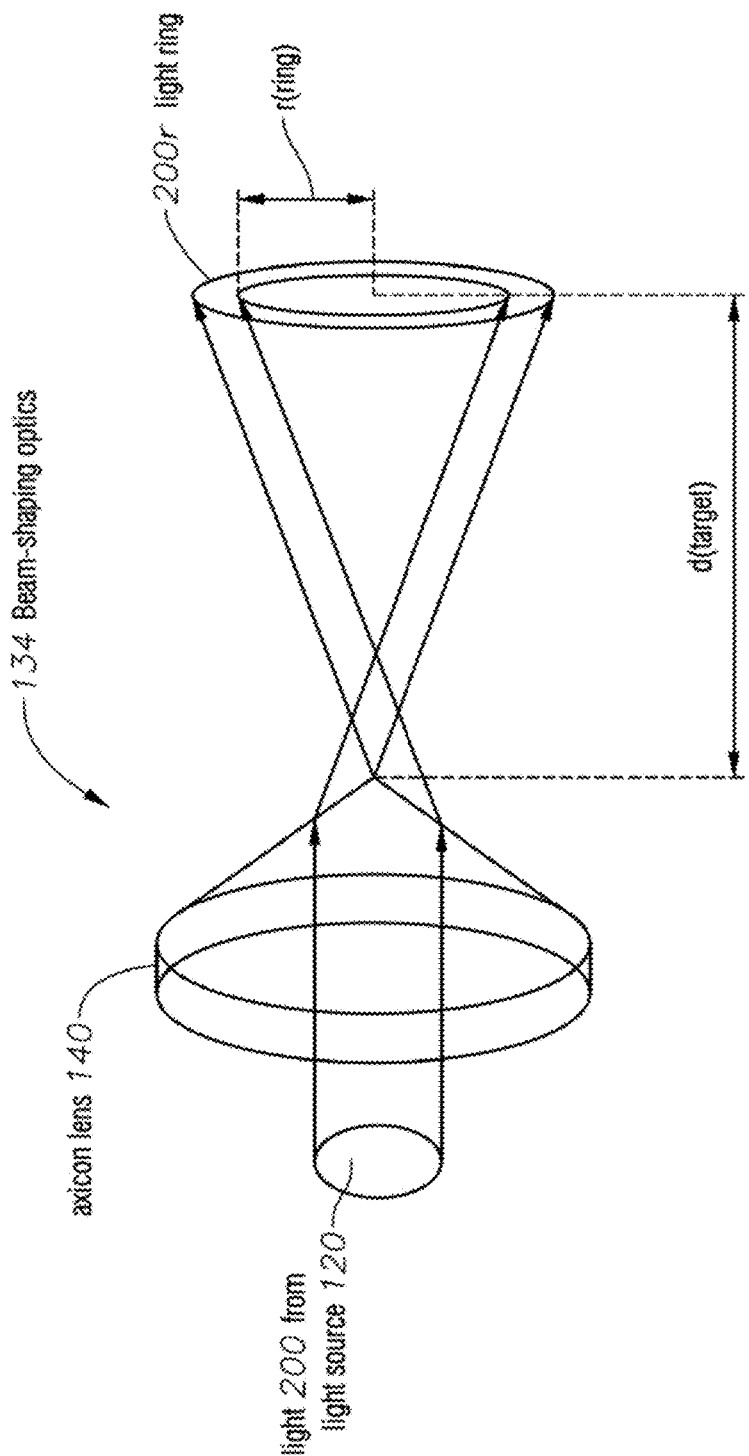
Figure 7C:
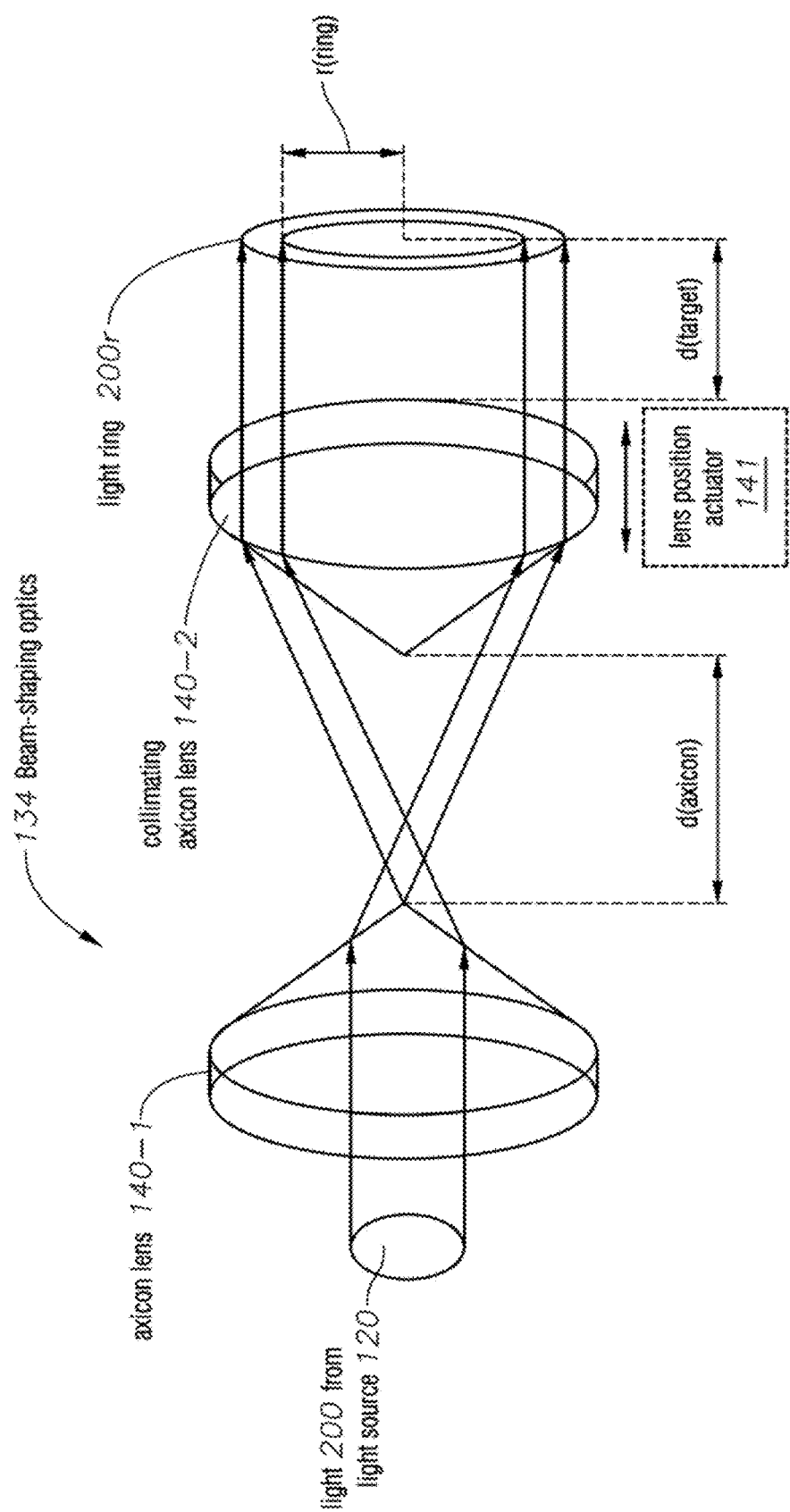
Figure 7D:
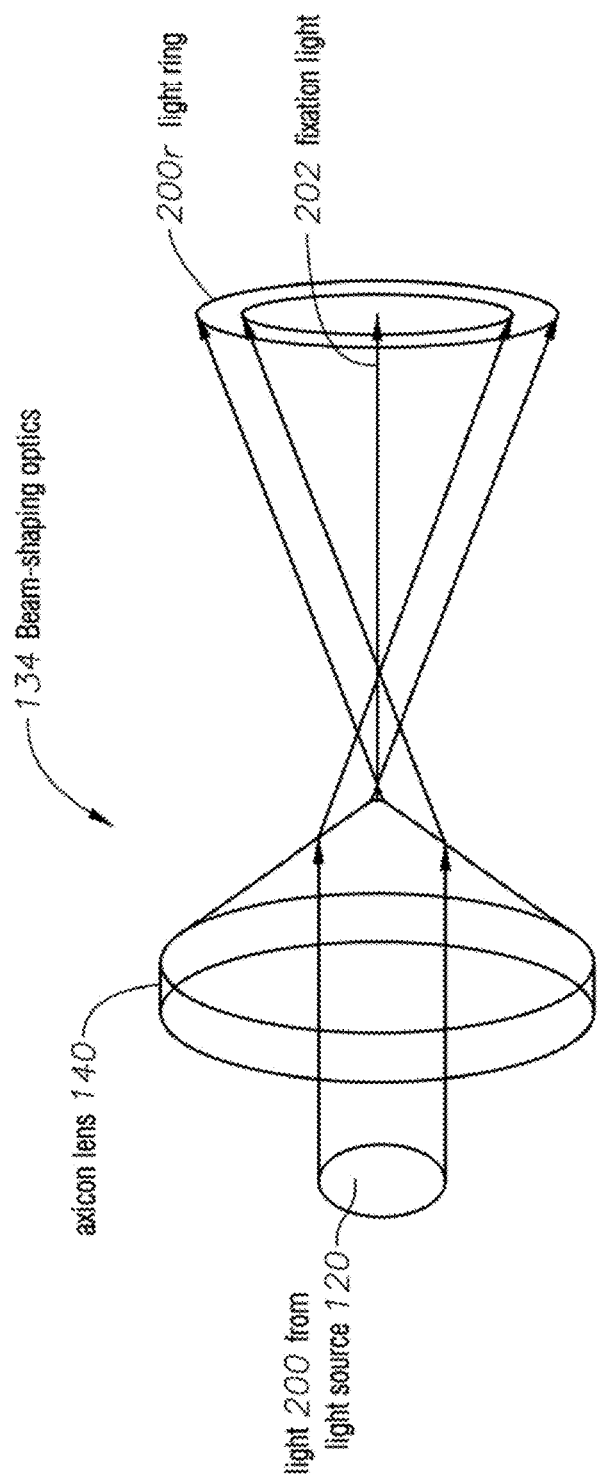
Figure 8A:
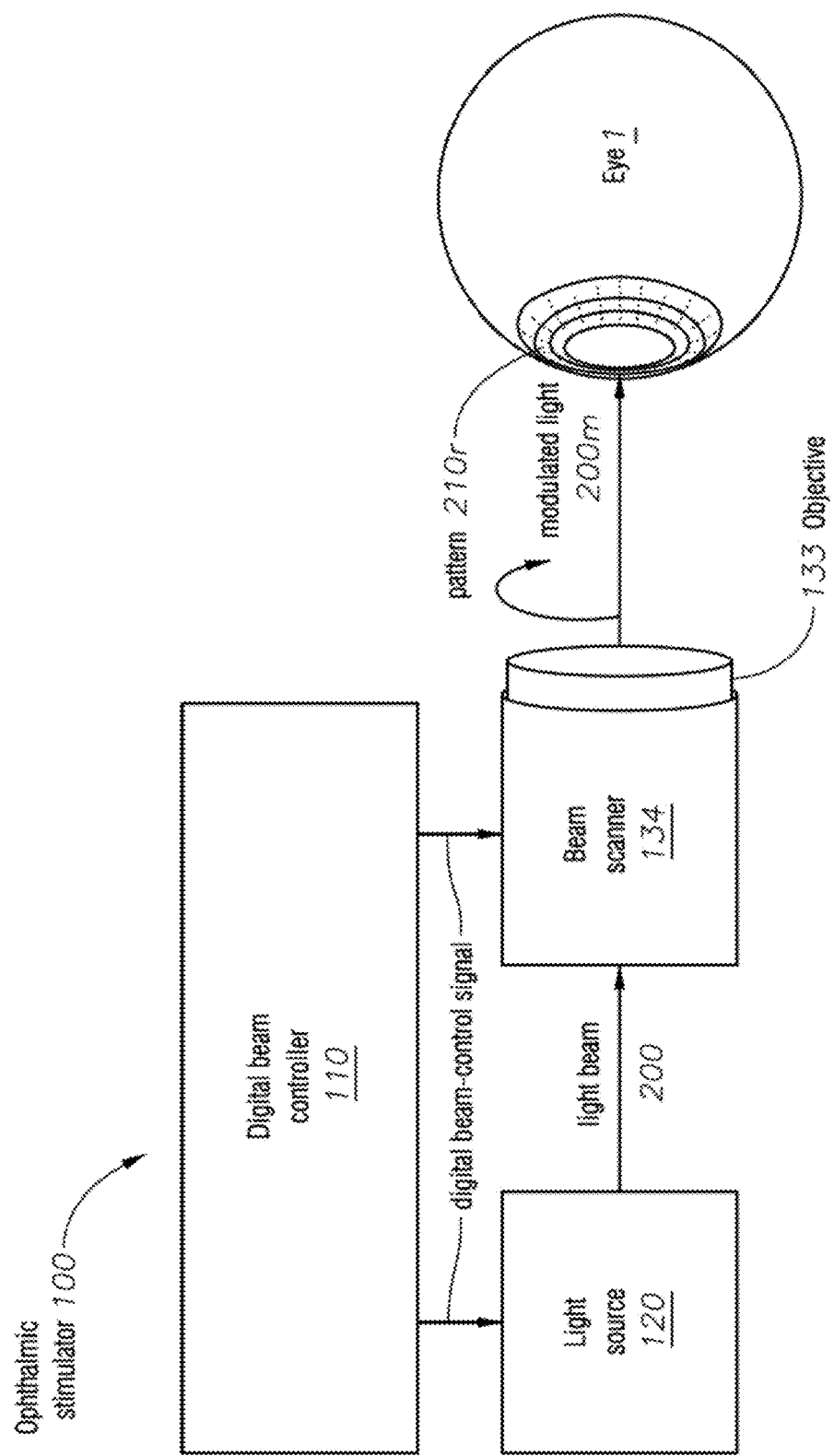
FIGS. 8A-B illustrate embodiments of the ophthalmic stimulator 100 with a digital beam controller 110.
Figure 8B:
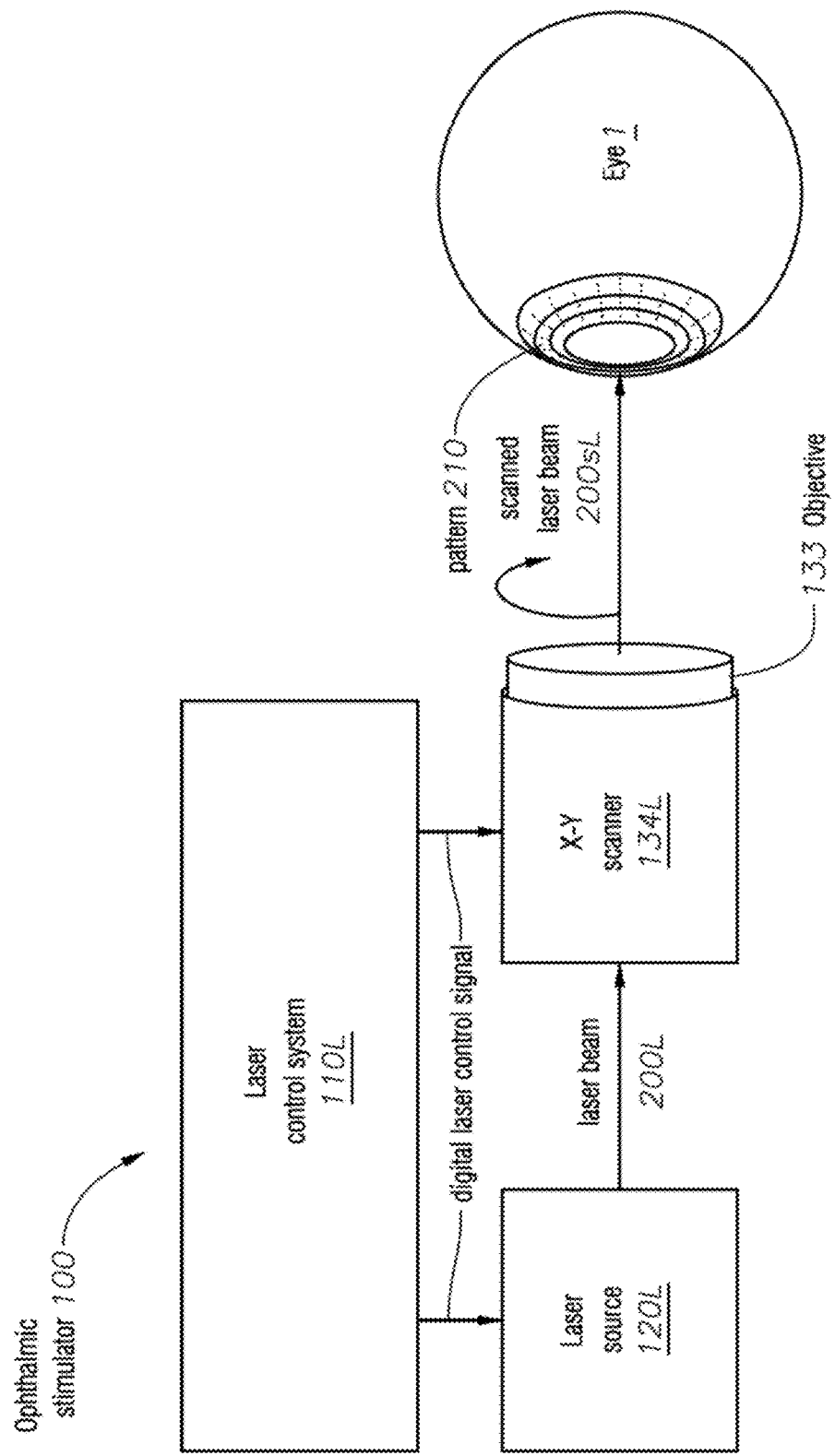
Figure 9A:
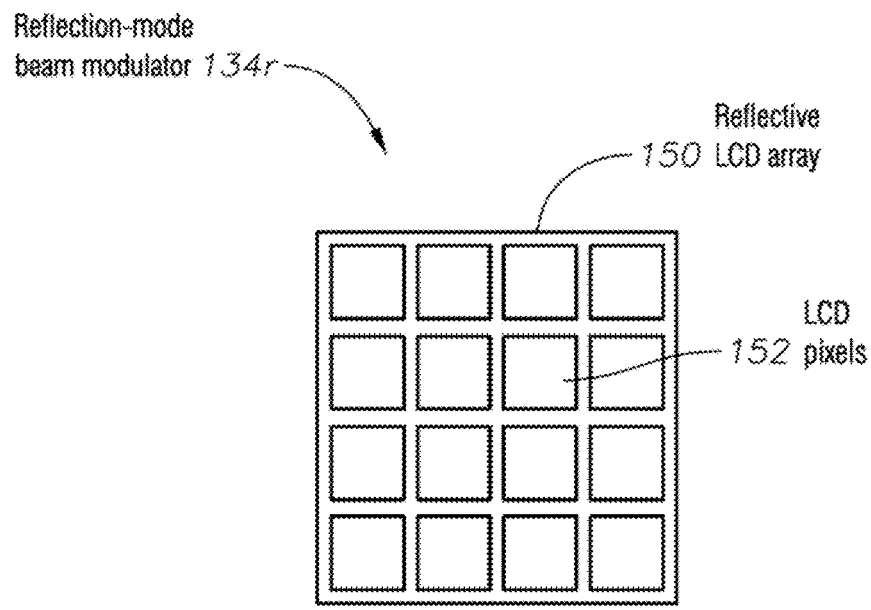
FIGS. 9A-E illustrate embodiments of the beam modulator 134.
Figure 9B:
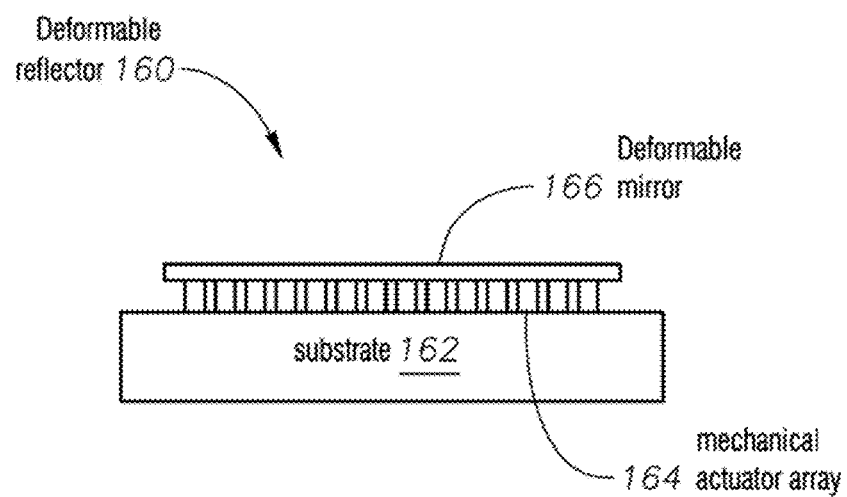
Figure 9C:
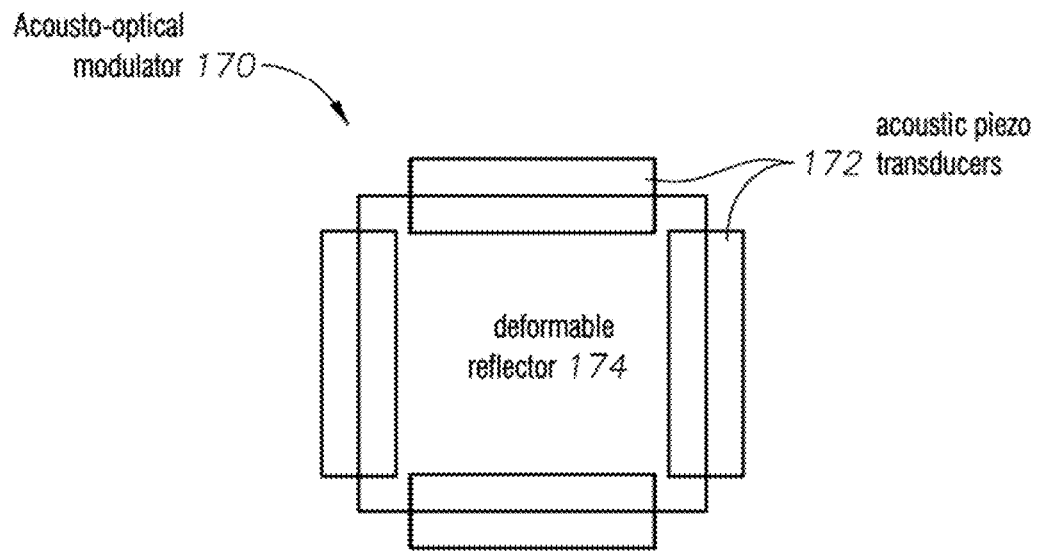
Figure 9D:
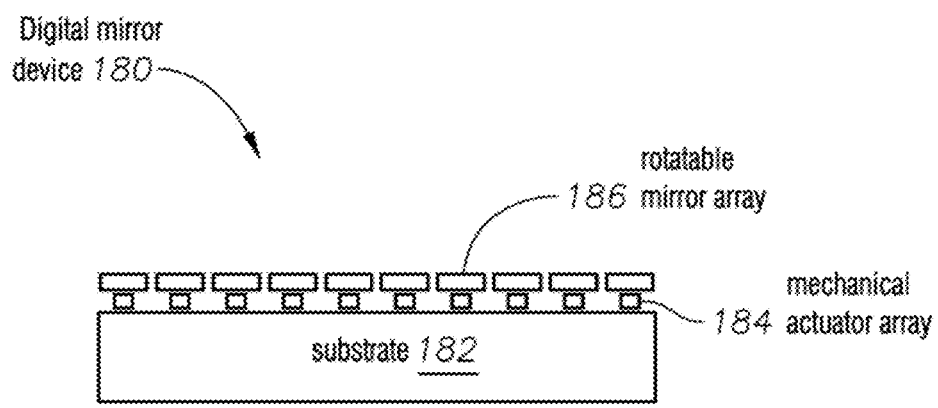
Figure 9E:
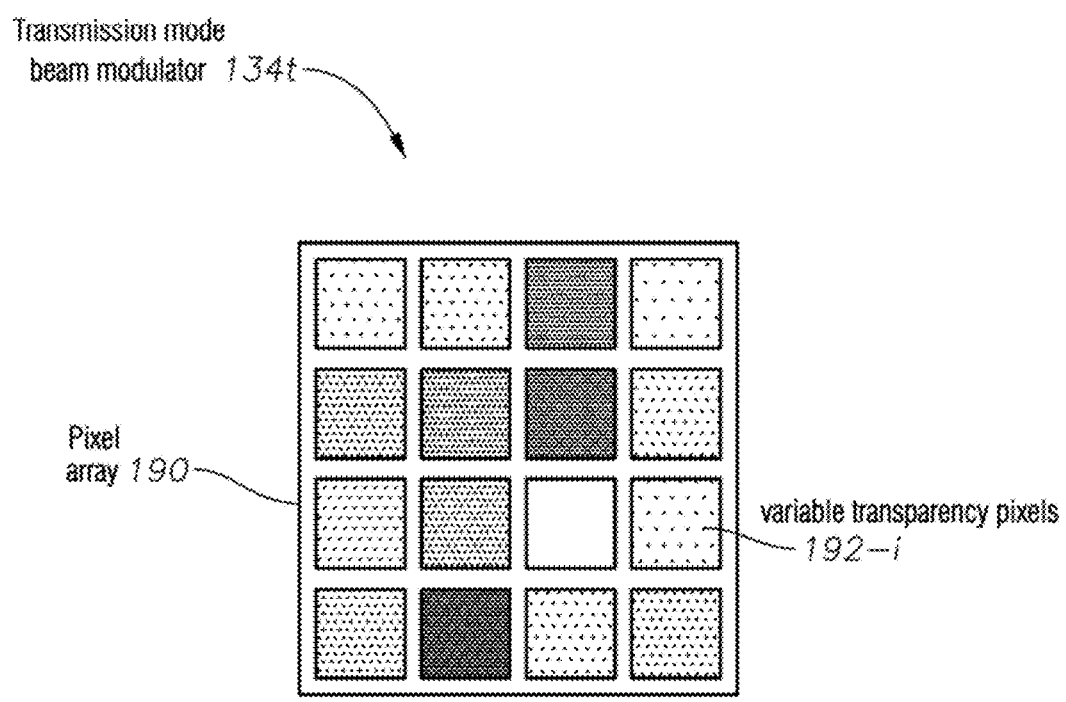

FIGS. 6C-D also show a feedback system 116. This system will be described in detail below.

Figure 10:
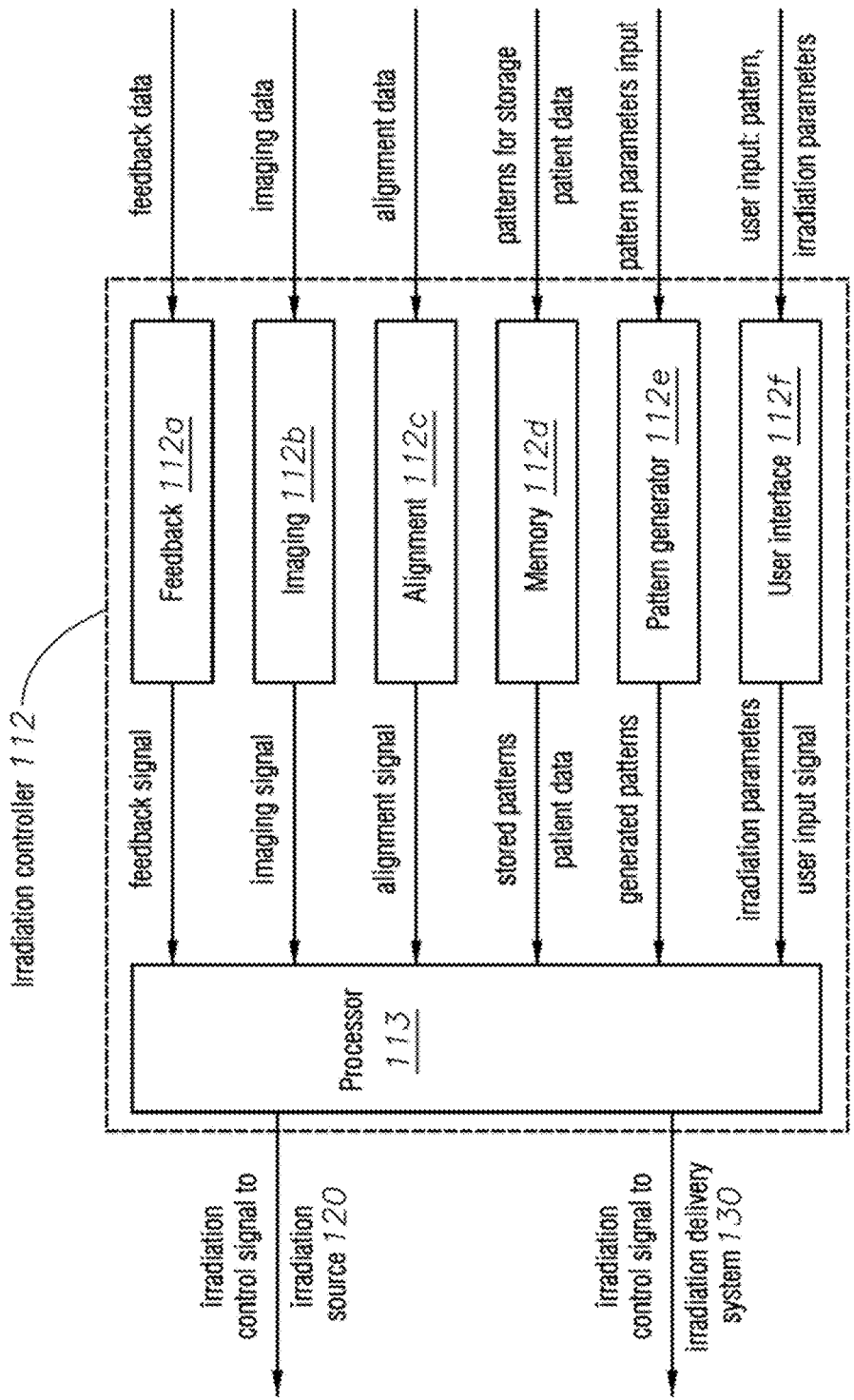
FIG. 10 illustrates an irradiation controller 112.

FIG. 10 illustrates that the irradiation controller 112 can include a number of blocks. These blocks can be implemented as a dedicated processor or circuitry, or can be implemented as a software, code, program, or application, implemented on a computer of the irradiation controller 112, or a combination of hardware and software blocks. In various embodiments, the irradiation controller 112 can include:

- a feedback block 112a, to receive feedback data and to send a feedback signal to a processor 113;
- an imaging block 112b, to receive imaging data and to send an imaging signal to the processor 113;
- air alignment block 112c, to receive alignment data and to send an alignment signal to the processor 113;
- a memory block 112d, to receive patterns for storage and patient data, to store algorithms and codes, and to send stored patterns, patient data, or executable algorithms to the processor 113;
- a pattern generator block 112e, to receive pattern parameters and to send generated patterns to the processor 113;
- a user interface block 112f, to receive a user input, for example through a user interface 118, that can be patterns, commands, and irradiation parameters, and to send the received patterns, commands and irradiation data as a user input signal to the processor 113.

Each of these blocks can receive their input from corresponding hardware blocks, such as sensors, controllers, hardware blocks and user interfaces. For example, the feedback block 112a can be a dedicated circuitry that receives the feedback data from the feedback system 116, as described below. The imaging block 112b can be a software algorithm, implemented on a processor that receives the imaging data from the imaging system 114 that can include a CCD camera, a video monitor, or a surgical microscope.

In response to signals, received from any of the blocks 112a-f, the processor 113 can send an irradiation control signal to the irradiation source 120, or to the irradiation delivery system 130, or to both.

In some detail, in embodiments of the ophthalmic stimulator 100 the irradiation control system 110 can include the memory 112d, and the generating the irradiation control signal can include recalling stored data from the memory 112d, representing at least one of an irradiation pattern and patient data, and generating the irradiation control signal to control the irradiation delivery system 130 to deliver the patterned irradiation 200p to the iris 11 in accordance with the recalled stored data.

In embodiments, the irradiation control system 110 can include a pattern generator; and the generating the irradiation control signal can include generating an electronic representation of the irradiation pattern 210; and generating the irradiation control signal to control the irradiation delivery system 130 to deliver the patterned irradiation 200p with the generated irradiation pattern 210.

Returning to the medial effects and treatments, embodiments of the ophthalmic stimulator 100 can cause a temporary constriction of the pupil 13 of the eye that includes an at least 5% reduction of a radius of the pupil 13 that lasts less than one hour. In some cases, the reduction of the radius of the pupil can last for a time interval more than one hour and less than one day. In other embodiments, the temporary constriction of the pupil of the eye includes an at least 5% reduction of the radius of the pupil that lasts for a time interval between one day and one week; or between one week and one month; or between one month and three months; or between three months and one year.

Each of these time intervals has their own medical and patient advantages. The longer the pupil constriction lasts, the less often the treatment may need to be applied, which can be preferred by patients. Also, the overall paradigm of use of the ophthalmic stimulator 100 depends on the duration of the constriction. Stimulators that constrict a pupil for a month or longer can be deployed in the offices of ophthalmologists, and patients can schedule regular visits for re-constriction treatments on a monthly basis. Stimulators that constrict the pupil for a day or longer could be tabletop systems that the individual patients buy, or lease, and they self-administer the treatment, for example, as part of a daily routine. Finally, stimulators that constrict the pupil for an hour, or for a few hours, can be mobile systems which the patient can carry with themselves and apply the treatment on demand. Obviously, stimulators operated by untrained patients have to have much more robust safety, monitoring and control systems to prevent undesirable medical outcomes. In sum, embodiments that constrict the pupil for different time intervals can offer very different medical outcomes, may be operated by very different personnel, and may need very different safety, monitoring and control systems.

Figure 11:
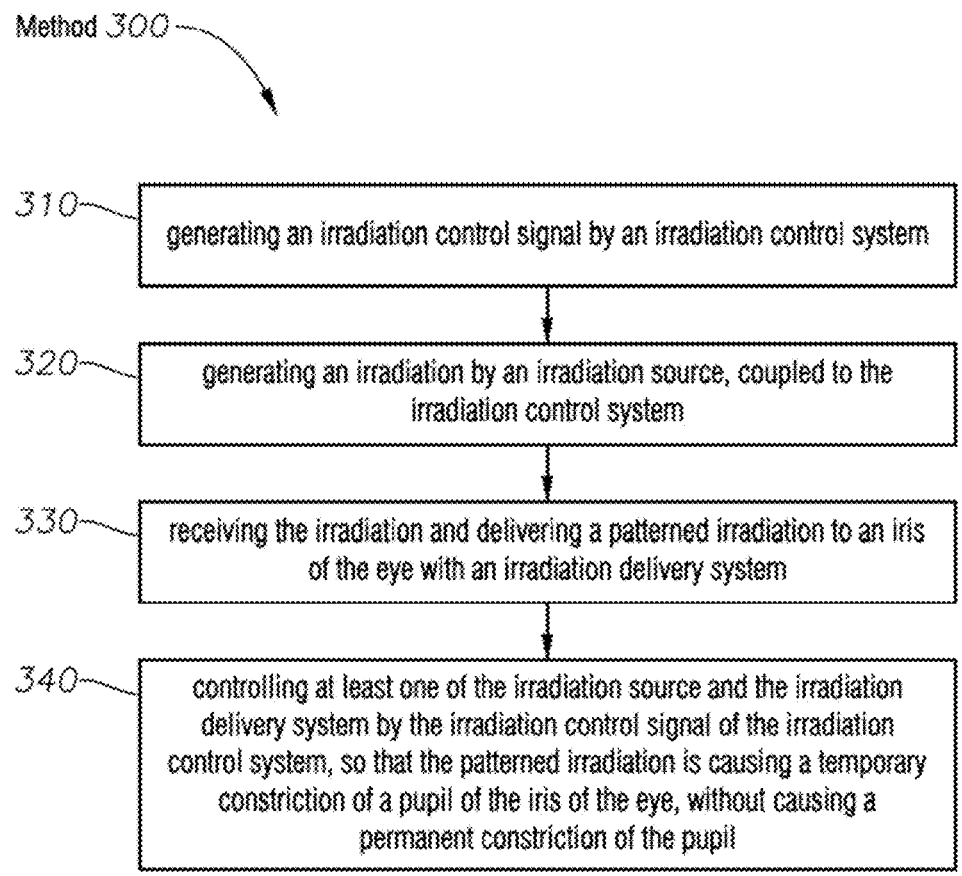
FIG. 11 illustrates steps of the method 300.

FIG. 11 illustrates embodiments of a method 300, related for the preceding description, for temporarily constricting a pupil 13 of an eye by an ophthalmic stimulator 100. The method 300 includes:

- generating 310 an irradiation control signal by an irradiation control system 110;
- generating 320 an irradiation 200 by an irradiation source 120, coupled to the irradiation control system 110;
- receiving 330 the irradiation 200, and delivering 332 a patterned irradiation 200p to an iris 11 of the eye with an irradiation delivery system 130; and
- controlling 340 at least one of the irradiation source 120 and the irradiation delivery system 130 by the irradiation control signal of the irradiation control system 110 so that the patterned irradiation is causing a temporary constriction of the pupil of the eye, without causing a permanent constriction of the pupil.

In embodiments, the generating 320 the irradiation 200 can include generating a light beam, an electromagnetic irradiation, a LED light, a narrow-band light, a broad-band light, an infrared beam, an incoherent light, a radio-frequency beam, or a sound by the irradiation source 120. Another class of irradiation sources 120 can include a coherent light source, a laser beam, a continuous wave laser beam, or a pulsed laser beam. Marked differences between the preceding incoherent irradiation sources and the just-listed coherent and laser sources will be discussed below.

The delivering 332 of the patterned irradiation 200p can include patterning the irradiation 200 by at least one of a pattern generator 112e, an optical beam shaper 132, a patterning optics, a beam profiler, a beam scanner 134, and a digitally controlled irradiation optics.

In embodiments, the causing, the temporary constriction of the pupil can include creasing a temperature of a treatment region of the iris to a range of 45-60 degrees Celsius. In some embodiments, the temperature of the treatment region of the iris can be raised into a range of 50-55 degrees Celsius.

FIG. 10 illustrates, that in some embodiments of the method 300, the irradiation control system 110 can include an imaging system 114, in some cases with a corresponding imaging block 112b in the irradiation controller 112, and a user interface 118, in some cases with a corresponding user interface block 112f in the irradiation controller 112. In these embodiments, the generating 310 of the irradiation control signal can include generating an image of the iris 11 of the eye with the imaging system 114 for a user, receiving an image-based input from the user through the user interface 118, and generating the irradiation control signal to control the irradiation delivery system 130 to deliver the patterned irradiation 200p in accordance with the received input. In embodiments, the patterned irradiation 200p can impact the iris in a ring pattern 210; and the image-based input can be an inner radius Rp(inner) and an outer radius Rp(outer) of the ring pattern 210, selected by the user.

In some embodiments of the method 300, the irradiation control system 110 can include an imaging system 114, and an image processor 114ip, in some cases implemented in the imaging block 112b of the irradiation controller 112. The generating 310 of the irradiation control signal can include generating an image of the iris of the eye with the imaging system 114 for the image processor 114ip; processing the image of the iris and generating an image-based input by the image processor 114ip; receiving the image-based input from the image processor 114ip; and generating 310 the irradiation control signal to control the irradiation delivery system 130 to deliver the patterned irradiation 200p in accordance with the received image-based input. In some designs, the patterned irradiation 200p can impact the iris 11 in a ring pattern 210; and the image-based input can be an inner radius Rp(inner) and an outer radius Rp(outer) of the ring pattern.

In some embodiments of the method 300, the irradiation control system 110 can include an alignment system 135, in some cases with its alignment block 112c in the irradiation controller 112; and the generating 310 of the irradiation control signal can include processing alignment data with the alignment system 135, and generating the irradiation control signal to control the irradiation delivery system 130 to deliver the patterned irradiation 200p to the iris in a pattern 210 aligned with the pupil 13 of the iris 11.

In some embodiments of the method 300, the processing alignment data can include generating an image of the iris with an imaging system 114, and overlaying an alignment pattern 138 on the image, in some cases with the alignment block 112c, or with the image processor 114ip; and the generating 310 the irradiation control signal can include generating a misalignment warning signal, or generating an alignment-guidance signal.

In some embodiments, the irradiation control system 110 can include a memory block 112d; and the generating the irradiation control signal 310 can include recalling stored data from the memory block 112d, representing at least one of an irradiation pattern 210 and patient data; and generating 310 the irradiation control signal to control the irradiation delivery system 130 to deliver the patterned irradiation 200p to the iris 11 in accordance with the recalled stored data. In some designs, the irradiation control system can include the pattern generator 112e; and the generating 310 of the irradiation control signal can include generating the irradiation pattern 210; and generating the irradiation control signal to control the irradiation delivery system 130 to deliver the patterned irradiation 200p with the generated irradiation pattern 210.

Some embodiments of the method 300 can include acquiring and analyzing patient data, selecting a treatment region based on the analyzing of the patient data; and delivering the patterned irradiation 200p to the selected treatment region. A notable embodiment of this step is the ophthalmologist analyzing patient data and deciding whether the treatment radiation shall be applied to the radial dilator muscles 30, or to the circular sphincter muscles 40. This analysis and decision can involve selecting the appropriate treatment parameters among the large number of treatment parameters described previously.

In some cases, the selecting the treatment region can include selecting a ring pattern 210r with an inner radius Rp(inner) larger than R(sphincter), a radius of a region of the circular sphincter muscles 40.

In some cases, the selecting the treatment region can include selecting a ring pattern 210r with an outer radius Rp(outer) smaller than R(sphincter), the radius of a region of the circular sphincter muscles 40.

Some embodiments of the method 300 can include controlling the irradiation source 120, or the irradiation delivery system 130, or both, so that the patterned irradiation 200p is causing a temporary constriction of the pupil of the eye that includes an at least 5% reduction of a radius of the pupil that lasts less than one hour.

In some cases, the temporary constriction of the pupil can last between one hour and one day. In some cases, the temporary constriction of the pupil can last between one day and one week; in some cases between one week and one month; in some cases between one month and three months; and in some cases between three months and one year. The medical, patient, implementation, and safety differences between embodiments involving temporary constrictions of different duration have been discussed earlier.

The ophthalmic stimulators 100 described up to now shared a common trait: they caused a temporary constriction of the pupil.

FIG. 5B illustrates a distinct class of permanent ophthalmic stimulators 100' that can cause a long-term, or even a permanent constriction of the pupil. These ophthalmic stimulators 100' share some of the major engineering elements with the temporary constriction stimulators 100, but have different medical modes of action, different irradiation sources, and stronger safety systems, among others.

In some embodiments, an ophthalmic stimulator 100' for constricting a pupil of an eye can include an irradiation control system 110', to generate an irradiation control signal; an irradiation source 120', coupled to the irradiation control system 110', to generate an irradiation 200'; and an irradiation delivery system 130', coupled to the irradiation control system 110', to receive the irradiation 200' from the irradiation source 120', and to deliver a patterned irradiation 200p' to the iris 11 of the eye 1; wherein the irradiation control system 110' controls the irradiation source 120', or the irradiation delivery system 130', or both, with the irradiation control signal so that the patterned irradiation 200p' causes a long-term constriction of the pupil of the eye.

In a class of the ophthalmic stimulator 100', the irradiation source 120' can include an incoherent light source, such as a lamp, a LED, an infrared light source, a radiofrequency source, an electromagnetic source and a sound source. In another class, the irradiation source 120' can include a coherent light source, such as laser, a pulsed laser and a continuous wave laser. There are substantial differences between irradiation sources that employ incoherent light sources and those that employ coherent light sources, as discussed above.

In some embodiments, the irradiation delivery system 130' can include an optical beam shaper and a patterning optics.

In some embodiments, the ophthalmic stimulator 100' can be configured to increase a temperature of a treatment region of the iris to a range of 50-80 degrees Celsius. In some embodiments, the ophthalmic stimulator 100' can be configured to increase a temperature of the treatment region of the iris to a range of 55-70 degrees Celsius.

Some embodiments of the ophthalmic stimulator 100' can cause a long-term constriction of the pupil that lasts longer than a year. In some cases, the ophthalmic stimulator 100' can be designed to cause an irreversible change in the iris of the eye. This long-term, or permanent, change can be a change of the length, or spatial extent, of the treated muscle tissue. In other cases, it can be a reduced, or enhanced, elasticity, or flexibility. In some cases, it can be an altered stiffness. In some cases, it can be an altered reactivity to stimuli.

The ophthalmic stimulator 100' achieves the long-term reduction of constriction of the pupil by applying the irradiation 200' with treatment parameters critically different from the ones used by the temporary stimulator 100. The critical difference can be one of many factors that cause permanent, or long-term constriction of the pupil, including the followings. Beams with wavelength short enough to cause permanent change. Beams with intensity per area high enough to cause long-term change. Beams with total deposited energy high enough to cause permanent change. Beams with treatment times long enough to cause permanent change. Beams with beam pulses long enough, and frequencies high enough to cause permanent change. Which specific parameters are sufficient to make the change permanent is patient specific and is selected by the surgeon.

In some embodiments, the irradiation control system 110' can include an imaging system 114' and a user interface 118'. In these embodiments, the irradiation control system 110' can generate the irradiation control signal by generating an image of the iris of the eye with the imaging system 114' for a user, receiving, an image-based input from the user through the user interface 118', and generating the irradiation control signal to control the irradiation delivery system 130' to deliver the patterned irradiation 200p' in accordance with the received input.

Some of the engineering details of the permanent ophthalmic stimulator 100' are analogous to that of the temporary ophthalmic stimulator 100'. To contain the length of this document, some of these details of the stimulator 100' will not be provided with their own figures, but the corresponding figures in the description of the stimulator 100 will be referenced, with the understanding that those need to be modified to cause a long term, not temporary constriction of the pupil.

In some embodiments of the ophthalmic stimulator 100', the irradiation control system 110' can include an alignment system 135'; and the irradiation control system 110' can generate the irradiation control signal by processing alignment data with the alignment system 135', and generating the irradiation control signal to control the irradiation delivery system 130' to deliver the patterned irradiation 200p' to the iris in a pattern 210, aligned with a pupil 13 of the iris 11.

Next, a related method 300' will be described for causing a long-term constriction of a pupil of an eye by the ophthalmic stimulator 100'. The method 300' can include the following steps.

generating 310' an irradiation control signal by an irradiation control system 110';

generating 320' an irradiation by an irradiation source 120', coupled to the irradiation control system 110';

receiving 330' the irradiation and delivering a patterned irradiation to an iris of the eye with an irradiation delivery system 130'; and controlling 340 at least one of the irradiation source 120' and the irradiation delivery system 130' by the irradiation control signal of the irradiation control system 110' so that the patterned irradiation causes a long-term constriction of the pupil of the eye.

In the method 300', the causing the long-term constriction of the pupil can include increasing a temperature of a treatment region of the iris to a range of 50-80 degrees Celsius. In some cases, the method 300' can include increasing a temperature of the treatment region of the iris to a range of 55-70 degrees Celsius. While these ranges have some overlap with temperature ranges described in relation to the temporary stimulator 100, for a particular patient the temperature range where the constriction is temporary can be quite well separated from the temperature range, where the constriction is permanent. For example, for a particular patient, temperatures in the range of 50-55 C may constrict the pupil for a day or less; temperatures in the 55-60 C range may cause the pupil to constrict for a time between a week and a month, temperatures in the 60-65 C range can cause the pupil to constrict for a time between a month and a year, and temperatures in the 65-70 C range may cause the pupil to constrict for a time longer than a year. These long-term changes can very well be associated with an irreversible change in the iris of the eye.

As before, in some embodiments of the method 300' the irradiation control system 110' can include an imaging system 114' and a user interface 118'; and the generating the irradiation control signal can include generating an image of the iris of the eye with the imaging system 114' for a user, receiving an image-based input from the user through the user interface 118', and generating the irradiation control signal to control the irradiation delivery system 130' to deliver the patterned irradiation 200p' in accordance with the received input.

In some embodiments of the method 300', the irradiation control system 110' can include an alignment system 135'; and the generating the irradiation control signal can include processing alignment data with the alignment system 135', and generating the irradiation control signal to control the irradiation delivery system 130' to deliver the patterned irradiation 200p' to the iris in a pattern 210 aligned with a pupil of the iris.

As discussed, the ophthalmologist operating the stimulator 100' can analyze several factors when practicing the method 300'. The analysis can include the determination what treatment parameters to use to achieve a long-term or permanent constriction change, to go beyond the previously described temporal changes. The analysis can also be focused at which treatment regions to irradiate. As discussed before, some vision-improvement goals can be better achieved by heat-treating the radial dilator muscles 30, others by heat-treating the circular sphincter muscles 40.

Both of these analyses can involve acquiring and analyzing patient data. In a typical example, a patient may have used the temporary ophthalmic stimulator 100 by practicing the method 300 repeatedly and for an extended period, and may have grown comfortable with its effect to the degree that she/he decided to make the constriction of the pupil permanent. During these preceding temporary treatments, the irradiation controller 110 of the stimulator 100, or its operator may have acquired and collected a substantial amount of data about the particular patient. An ophthalmologist, who is planning administering a higher energy irradiation by practicing the method 300' with a permanent ophthalmic stimulator 100' to permanently change the constriction of the pupil, may evaluate and analyze the data that was collected during the previous, repeated temporary constrictions of the pupil of this particular patient. This analysis can be followed by selecting a treatment region based on the analyzing of the patient data; and delivering the patterned irradiation 200p' to the selected treatment region to cause the long-term constriction of the pupil.

The invention claimed is:

1. An ophthalmic stimulator for temporarily constricting a pupil of a presbyopic eye, comprising:
   an irradiation control system, to generate an irradiation control signal;
   the irradiation control system comprises an imaging system;
   an irradiation source, coupled to the irradiation control system, to generate an irradiation; and
   an irradiation delivery system, coupled to the irradiation control system,
      to receive the irradiation from the irradiation source, and
      to deliver a patterned, non-scanning irradiation to an iris of the eye; wherein
   the irradiation control system is configured to generate the irradiation control signal by generating an image of the iris of the eye with the imaging system, and
   the irradiation control system controls at least one of the irradiation source and the irradiation delivery system with the irradiation control signal so that the patterned irradiation causes a temporary constriction of the pupil of the eye, including an at least 5% reduction of a radius of the pupil that lasts between one hour and one day, without causing a permanent constriction of the pupil, wherein
   parameters of the irradiation source and the irradiation delivery system are configured in a combination to cause the temporary constriction of the pupil including:
   a wavelength of the irradiation source in a range of 400-4,000 nm;
   a power density of the patterned irradiation in a range of 0.1-1000 mW/cm$^2$;
   a total energy, deposited by the patterned irradiation in a range of 10 µJ-10 J;
   a time period of delivering the irradiation is in a range of 1-100 seconds; and
   the ophthalmic stimulator is configured to increase a temperature of a treatment region of the iris into a range of 45-60 degrees Celsius with the irradiation.

2. The ophthalmic stimulator of claim 1, wherein:
   the irradiation source includes at least one incoherent light source, selected from a lamp, a LED, an infrared source, a radiofrequency source, and an electromagnetic radiation source,
   to generate at least one of a light beam, an electromagnetic irradiation, an infrared beam, a LED light, a radiofrequency radiation, and a sound.

3. The ophthalmic stimulator of claim 1, wherein:
   the irradiation source includes at least one coherent light source, selected from a laser, a pulsed laser and a continuous wave laser,
   to generate at least one of a laser beam and a pulsed laser beam.

4. The ophthalmic stimulator of claim 1, wherein:
   the ophthalmic stimulator is configured to increase a temperature of the treatment region of the iris to a range of 50-55 degrees Celsius.

5. The ophthalmic stimulator of claim 1, wherein:
   the irradiation control system comprises and a user interface; and
   the irradiation control system generates the irradiation control signal by
      generating an image of the iris of the eye with the imaging system for a user,
      receiving an image-based input from the user through the user interface, and
      generating the irradiation control signal to control the irradiation delivery system to deliver the patterned irradiation in accordance with the received image-based input.

6. The ophthalmic stimulator of claim 4, wherein:
   the patterned irradiation impacts the iris in a ring pattern; and
   the image-based input is a selection of at least one of an inner radius and an outer radius of the ring pattern.

7. The ophthalmic stimulator of claim 1, wherein:
   the irradiation control system comprises an imaging system with an image processor; and
   the irradiation control system generates the irradiation control signal by
      generating an image of the iris of the eye with the imaging system for the image processor,
      receiving an image-based input from the image processor, and
      generating the irradiation control signal to control the irradiation delivery system to deliver the patterned irradiation in accordance with the received image-based input.

8. The ophthalmic stimulator of claim 7, wherein:
   the patterned irradiation impacts the iris in a ring pattern; and
   the image-based input is a selection of at least one of an inner radius and an outer radius of the ring pattern.

9. The ophthalmic stimulator of claim 1, wherein:
   the irradiation control system comprises an alignment system; and
   the irradiation control system generates the irradiation control signal by
      processing alignment data with the alignment system, and
      generating the irradiation control signal to control the irradiation delivery system to deliver the patterned irradiation to the iris in a pattern aligned with the pupil of the eye.

10. The ophthalmic stimulator of claim 9, wherein:
    the processing alignment data includes:
       generating an image of the iris with an imaging system, and
       overlaying an alignment pattern on the generated image; and
    the generating the irradiation control signal includes at least one of
       generating a misalignment warning signal, and
       generating an alignment-guidance signal.

11. The ophthalmic stimulator of claim 1, wherein:
    the irradiation control system comprises a memory; and
    the generating the irradiation control signal includes:
       recalling stored data from the memory, representing at least one of an irradiation pattern and patient data, and generating the irradiation control signal to control the irradiation delivery system to deliver the patterned irradiation to the iris in accordance with the recalled stored data.

12. The ophthalmic stimulator of claim 1, wherein:

the irradiation control system comprises a pattern generator; and the generating the irradiation control signal includes:
  generating an irradiation pattern; and
  generating the irradiation control signal to control the irradiation delivery system to deliver the patterned irradiation with the generated irradiation pattern.

13. The ophthalmic stimulator of claim 1, wherein:

the irradiation delivery system, is configured to deliver a patterned irradiation to the iris of the eye in a ring pattern with an inner radius larger than a radius of a region of the circular sphincter muscles.

14. The ophthalmic stimulator of claim 1, wherein:

the irradiation delivery system, is configured to deliver a patterned irradiation to the iris of the eye in a ring pattern with an outer radius smaller than a radius of a region of the circular sphincter muscles.

* * * * *